US012712072B2

(12) United States Patent
Sullivan et al.

(10) Patent No.: US 12,712,072 B2
(45) Date of Patent: Aug. 18, 2026

(54) ADAPTIVE TROUBLESHOOTING FOR A MEDICAL DEVICE

(71) Applicant: West Affum Holdings Designated Activity Company, Dublin (IE)

(72) Inventors: Joseph L. Sullivan, Kirkland, WA (US); Mark P. Moore, Redmond, WA (US); Steven E. Sjoquist, Lynnwood, WA (US); Leo J. Gilbert, Kirkland, WA (US); Hema A. Ingle, Woodinville, WA (US); Jonathan P. Niegowski, Issaquah, WA (US); Zoie R. Brent, Portland, OR (US)

(73) Assignee: West Affum Holdings DAC, Dublin (IE)

( * ) Notice: Subject to any disclaimer, the term of this patent is extended or adjusted under 35 U.S.C. 154(b) by 246 days.

(21) Appl. No.: 18/170,435

(22) Filed: Feb. 16, 2023

(65) Prior Publication Data

US 2023/0260642 A1 Aug. 17, 2023

Related U.S. Application Data

(60) Provisional application No. 63/311,179, filed on Feb. 17, 2022.

(51) Int. Cl.
*G16H 40/40* (2018.01)
*A61N 1/39* (2006.01)
*G06Q 30/016* (2023.01)

(52) U.S. Cl.
CPC ........... *G16H 40/40* (2018.01); *A61N 1/3925* (2013.01); *G06Q 30/016* (2013.01)

(58) Field of Classification Search
None
See application file for complete search history.

(56) References Cited

U.S. PATENT DOCUMENTS 3,724,355 A 4/1973 Busch et al.
3,724,455 A 4/1973 Unger
(Continued)

FOREIGN PATENT DOCUMENTS

CN 105575070 A * 5/2016 ............. G08B 21/24
CN 106096230 A * 11/2016 ............. G16H 10/65
(Continued)

OTHER PUBLICATIONS

Heartstart MRx and XL AED Algorithm—Application Note, Jul. 2001, Edition 2 Philips Healthcare, USA.
(Continued)

*Primary Examiner* — Mamon Obeid
*Assistant Examiner* — Ashley Elizabeth Evans
(74) *Attorney, Agent, or Firm* — Lisa Benado; Propel IP Law, PLLC

(57) ABSTRACT

A medical device troubleshooting system is provided to interact with and assist a user in resolving operational problems with a medical device. The troubleshooting system may detect an operational problem with the medical device and initiate a troubleshooting session to output a series of different tailored prompts for a user to rectify the glitch. The user prompts are selected and presented in an adaptive manner based on patient specific factors. Selection of prompts and prompt presentation may be responsive to user actions, changes in the patient, and/or the condition of the operational problem. The troubleshooting system checks the condition of the operational problem after presentation of each user prompt and determines a next user prompt accordingly, or ends the session. When the operational problem persists after ending of the session, an external support resource may be contacted.

20 Claims, 8 Drawing Sheets

(56) References Cited

U.S. PATENT DOCUMENTS 4,583,524 A 4/1986 Hutchins
4,619,265 A 10/1986 Morgan et al.
4,666,432 A 5/1987 McNeish et al.
4,698,848 A 10/1987 Buckley
4,928,690 A 5/1990 Heilman et al.
4,955,381 A 9/1990 Way et al.
5,078,134 A 1/1992 Heilman et al.
5,228,449 A 7/1993 Christ et al.
5,348,008 A 9/1994 Bornn et al.
5,353,793 A 10/1994 Bornn
RE34,800 E 11/1994 Hutchins
5,394,892 A 3/1995 Kenny et al.
5,405,362 A 4/1995 Kramer et al.
5,429,593 A 7/1995 Matory
5,474,574 A 12/1995 Payne et al.
5,618,208 A 4/1997 Crouse et al.
5,662,690 A 9/1997 Cole et al.
5,708,978 A 1/1998 Johnsrud
5,741,306 A 4/1998 Glegyak et al.
5,782,878 A 7/1998 Morgan et al.
5,792,204 A 8/1998 Snell
5,902,249 A 5/1999 Lyster
5,913,685 A 6/1999 Hutchins
5,944,669 A 8/1999 Kaib
6,047,203 A 4/2000 Sackner et al.
6,065,154 A 5/2000 Hulings et al.
6,108,197 A 8/2000 Janik
6,148,233 A 11/2000 Owen et al.
6,201,992 B1 3/2001 Freeman
6,263,238 B1 7/2001 Brewer et al.
6,280,461 B1 8/2001 Glegyak et al.
6,287,328 B1 9/2001 Snyder et al.
6,304,780 B1 10/2001 Owen et al.
6,319,011 B1 11/2001 Motti et al.
6,334,070 B1 12/2001 Nova et al.
6,356,785 B1 3/2002 Snyder et al.
6,427,083 B1 7/2002 Owen et al.
6,437,083 B1 8/2002 Brack et al.
6,450,942 B1 9/2002 Lapanashvili et al.
6,529,875 B1 3/2003 Nakajima et al.
6,546,285 B1 4/2003 Owen et al.
6,671,545 B2 12/2003 Fincke
6,681,003 B2 1/2004 Linder et al.
6,762,917 B1 7/2004 Verbiest et al.
7,065,401 B2 6/2006 Worden
7,099,715 B2 8/2006 Korzinov
7,212,850 B2 5/2007 Prystowsky
7,559,902 B2 7/2009 Ting et al.
7,587,237 B2 9/2009 Korzinov
7,753,759 B2 7/2010 Pintor et al.
7,865,238 B2 1/2011 Brink
7,870,761 B2 1/2011 Valentine et al.
7,907,996 B2 3/2011 Prystowsky
7,941,207 B2 5/2011 Korzinov
7,974,689 B2 7/2011 Volpe et al.
8,135,462 B2 3/2012 Owen et al.
8,140,154 B2 3/2012 Donnelly et al.
8,369,944 B2 2/2013 Macho et al.
8,527,028 B2 9/2013 Kurzweil et al.
8,548,557 B2 10/2013 Garstka et al.
8,560,044 B2 10/2013 Kurzweil et al.
8,615,295 B2 12/2013 Savage et al.
8,644,925 B2 2/2014 Volpe et al.
8,676,313 B2 3/2014 Volpe et al.
8,706,255 B2 4/2014 Phillips et al.
8,742,349 B2 6/2014 Urbon et al.
8,897,860 B2 11/2014 Volpe et al.
8,904,214 B2 12/2014 Volpe et al.
8,965,500 B2 2/2015 Macho et al.
9,008,801 B2 4/2015 Kaib et al.
9,084,583 B2 7/2015 Mazar et al.
9,089,685 B2 7/2015 Sullivan et al.
9,119,547 B2 9/2015 Cazares et al.
9,131,901 B2 9/2015 Volpe et al.
9,132,267 B2 9/2015 Kaib
9,265,432 B2 2/2016 Warren et al.
9,345,898 B2 5/2016 Piha et al.
9,408,548 B2 8/2016 Volpe et al.
9,445,719 B2 9/2016 Libbus et al.
9,454,219 B2 9/2016 Volpe et al.
9,579,020 B2 2/2017 Libbus et al.
9,592,403 B2 3/2017 Sullivan
9,598,799 B2 3/2017 Shoshani et al.
9,675,804 B2 6/2017 Whiting et al.
9,724,008 B2 8/2017 Sullivan et al.
9,757,581 B2 9/2017 Sullivan
9,878,171 B2 1/2018 Kaib
9,895,105 B2 2/2018 Romem
9,901,741 B2 2/2018 Chapman et al.
RE46,926 E 7/2018 Bly et al.
10,076,656 B2 9/2018 Dar et al.
10,192,387 B2 1/2019 Brinig et al.
10,307,133 B2 6/2019 Kaib
10,463,867 B2 11/2019 Kaib et al.
10,589,110 B2 3/2020 Oskin et al.
10,599,814 B2 3/2020 Landrum et al.
11,083,906 B2 8/2021 Foshee
11,291,850 B2 * 4/2022 Pavel .................. A61N 1/3987
11,709,747 B2 * 7/2023 Hresko ............... G06F 11/3013
705/2
12,020,811 B2 * 6/2024 Pal ........................ G06F 16/951
2002/0181680 A1 12/2002 Linder et al.
2003/0158593 A1 8/2003 Heilman et al.
2005/0107833 A1 5/2005 Freeman et al.
2005/0107834 A1 5/2005 Freeman et al.
2006/0173499 A1 8/2006 Hampton et al.
2008/0312709 A1 12/2008 Volpe et al.
2009/0005827 A1 1/2009 Weintraub et al.
2010/0007413 A1 1/2010 Herleikson et al.
2010/0298899 A1 11/2010 Donnelly et al.
2011/0022105 A9 1/2011 Owen et al.
2011/0288604 A1 11/2011 Kaib et al.
2011/0288605 A1 11/2011 Kaib et al.
2012/0112903 A1 5/2012 Kaib et al.
2012/0144551 A1 6/2012 Guldalian
2012/0150008 A1 6/2012 Kaib et al.
2012/0158075 A1 6/2012 Kaib et al.
2012/0191476 A1 7/2012 Reid et al.
2012/0265265 A1 10/2012 Razavi et al.
2012/0283794 A1 11/2012 Kaib et al.
2012/0293323 A1 11/2012 Kaib et al.
2012/0302860 A1 11/2012 Volpe et al.
2012/0310315 A1 12/2012 Savage et al.
2013/0085538 A1 4/2013 Volpe et al.
2013/0144355 A1 6/2013 Macho et al.
2013/0231711 A1 9/2013 Kaib
2013/0245388 A1 9/2013 Rafferty et al.
2013/0274565 A1 10/2013 Langer et al.
2013/0317852 A1 11/2013 Worrell et al.
2013/0325078 A1 12/2013 Whiting et al.
2014/0012144 A1 1/2014 Crone
2014/0025131 A1 1/2014 Sullivan et al.
2014/0046391 A1 2/2014 Cowan et al.
2014/0070957 A1 3/2014 Longinotti-Buitoni et al.
2014/0163663 A1 6/2014 Poddar et al.
2014/0324112 A1 10/2014 Macho et al.
2014/0378812 A1 12/2014 Saroka et al.
2015/0039053 A1 2/2015 Kaib et al.
2015/0161554 A1 6/2015 Sweeney et al.
2015/0297135 A1 10/2015 Shoshani et al.
2015/0328472 A1 11/2015 Sullivan et al.
2016/0004831 A1 1/2016 Carlson et al.
2016/0076175 A1 3/2016 Rock et al.
2016/0076176 A1 3/2016 Rock et al.
2016/0082277 A1 3/2016 Foshee, Jr. et al.
2016/0113581 A1 4/2016 Amir et al.
2016/0256104 A1 9/2016 Romem et al.
2016/0283900 A1 9/2016 Johnson et al.
2017/0014073 A1 1/2017 Shoshani et al.
2017/0027469 A1 2/2017 Amir et al.
2017/0036066 A1 2/2017 Chahine
2017/0040758 A1 2/2017 Amir et al.
2017/0162840 A1 6/2017 Pendry
2017/0319862 A1 11/2017 Foshee, Jr. et al.

(56) References Cited

U.S. PATENT DOCUMENTS

| | | | | |
|---|---|---|---|---|
| 2017/0367591 | A1 | 12/2017 | Jorgensen | |
| 2018/0116537 | A1 | 5/2018 | Sullivan et al. | |
| 2018/0117299 | A1 | 5/2018 | Gustavson et al. | |
| 2018/0184933 | A1 | 7/2018 | Sullivan et al. | |
| 2018/0243578 | A1 | 8/2018 | Volosin | |
| 2018/0361165 | A1 | 12/2018 | Jaax et al. | |
| 2019/0030352 | A1 | 1/2019 | Sullivan et al. | |
| 2019/0076666 | A1 | 3/2019 | Medema | |
| 2019/0116896 | A1 | 4/2019 | Armour et al. | |
| 2019/0321650 | A1 | 10/2019 | Raymond et al. | |
| 2022/0245799 | A1 * | 8/2022 | Doctor | G05B 23/0216 |
| 2023/0259821 | A1 * | 8/2023 | Travalini | G06N 3/0455 706/12 |

FOREIGN PATENT DOCUMENTS

| | | | |
|---|---|---|---|
| DE | 102005060985 | A2 | 6/2007 |
| EP | 2305110 | A1 | 4/2011 |
| JP | 2005507747 | A | 3/2005 |
| JP | 2014500099 | A | 1/2014 |
| JP | 2014526282 | A2 | 10/2014 |
| WO | 9839061 | A1 | 9/1998 |
| WO | 2011/146448 | A1 | 11/2011 |
| WO | 2012/064604 | A1 | 5/2012 |
| WO | 2012/151160 | A1 | 11/2012 |
| WO | 2015/056262 | A1 | 4/2015 |
| WO | 2023107404 | A2 | 6/2023 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi: 10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

200

ADAPTIVE TROUBLESHOOTING FOR A MEDICAL DEVICE

CROSS REFERENCES TO RELATED APPLICATIONS

This application claims the benefit of the filing date of U.S. Provisional Patent Application No. 63/311,179 filed Feb. 17, 2022, the disclosure of which is hereby incorporated herein by reference for all purposes.

FIELD OF THE INVENTION

The present disclosure generally relates to a providing instructions for a user to troubleshoot a problem with a medical device.

BACKGROUND

Various medical devices can gather health related data about a patient. Some medical devices may include wearable portions that are worn by patients while the patient goes about day-to-day activities. For example, extended wear medical devices enable clinicians to gain a full picture of specific health aspects of a patient.

Some wearable medical devices can also provide treatment to the patient. For example, wearable devices used in cardiac monitoring may incorporate electrocardiogram (ECG) electrodes that detect electrical impulses of the heart when the heart beats. Electricity detected by electrodes is translated into a wavy graph line that is recorded. Certain medical-grade monitoring devices provide critical health information that may require immediate attention, for example, lifesaving alerts of cardiac conditions. Some medical devices can also automatically transmit appropriate shock energy to the patient to treat the patient on the fly based on sensor data about the patient.

It can be vital that wearable medical devices properly operate while in use. For example, improper positioning of a medical device, low power, or a malfunction of a component of the medical device could compromise data gathered and/or result in improper treatment to the patient.

Problems with proper functioning of equipment often need to be swiftly resolved. A patient or person at the site of the patient, such as a caretaker, can be situated to immediately rectify simple problems. It is advantageous to empower a user of the medical device, such as the patient, to resolve some problems without the need to call for technical support for any or every issue. Instructions to the user should be presented in a manner effective to assist diverse users in responding to a glitch in the medical device.

SUMMARY

A present medical device troubleshooting system (also referred to as a "troubleshooting system") is provided to enable user action to resolve an operational problem of the device. A user is provided with sequential user prompts having different instructions than instructions of other prompts in the troubleshooting session. The prompts are provided until a stopping event occurs. The troubleshooting system can employ various patient specific factors from patient specific data to adaptively select an appropriate user prompt, such as current patient status, predictive patient behavior, and patient traits. Operational problems with the medical device may involve issues with a wearable component or other aspects of the medical device that interfere with or has the potential to interfere with proper patient monitoring and/or treatment. User prompts van also be dynamically chosen during a troubleshooting session with changing circumstances of the patient.

In some implementations, a method is provided for troubleshooting a medical device in which signals are received from a sensor associated with the medical device, when such signals are available from the sensor. To detect an operational problem of one or more components of the medical device, the received signals are assessed or a determination is made that no signals are received. In response to detecting an operational problem, a troubleshooting session is initiated. The session includes receiving one or more patient specific factors and outputting a selected user prompt in plain language to assist a user in resolving the operational problem. A next user prompt that is outputted after an initial user prompt is different than prior user prompts in the troubleshooting session. The selected user prompts are based, at least in part, the one or more patient specific factors. The steps are iteratively repeated including the steps of assessing signals or determining no signals are received and outputting of the selected next user prompt until at least one stopping event occurs.

At times, the one or more patient specific factors employed in the method may include includes a patient current status determined by the medical device. The patient current status may be used as a basis for an output modality and/or output characteristic of the selected user prompts. The patient current status may also be used as a basis for selecting a first stored sequence of user prompts associated with a same or similar operational problem according to the method. The method may further include selecting a user prompt from the stored sequence. A second stored sequence of user prompts or a different next user prompt may be dynamically reselected based, at least in part, on a change in the patient current status during the troubleshooting session.

In some aspects of the method, an artificial intelligence (AI) model may be applied to output sequences of user prompts associated with various operational problems. The AI model may be trained at least in part, on global patient experience data. The outputted sequence of user prompts may be stored and a sequence of user prompts may be selected from the stored sequence of user prompts, based at least in part, on the one or more patient specific factors.

In some implementations of the method, the user prompt may be selected based, at least in part, on the one or more patient specific factors and an initial user prompt in the sequence of user prompts may be selected based on one or more prior successful user prompts in previous troubleshooting sessions for a same or similar operational problem by the patient.

A stopping event to end the troubleshooting session may include determining that the operational problem is resolved, a predefined time for the troubleshooting session is reached, or a threshold number of prompts are outputted without resolution of the operational problem. The stopping event may result in contacting an external support or instructing the user to contact the external support, where the operational problem persists.

A medical device troubleshooting system is also provided, which includes a medical device and may further include at least one sensor to monitor a parameter associated with health of a patient and to generate signals based on the monitored parameter. The system also includes at least one computing device having at least one processor configured for performing various steps. The steps may involve detecting an operational problem of one or more components of the medical device based on the signal. In response to the detected operational problem, a troubleshooting session may be initiated. Such session includes receiving one or more patient specific factors and outputting a selected user prompt to assist a user in resolving the operational problem. A next user prompt after an initial user prompt is different than prior user prompts in the troubleshooting session. The selected user prompt is based, at least in part, on the one or more patient specific factors. Some steps are iteratively repeated including the outputting of the selected next user prompt if the operational problem is determined to persist after each output of a next user prompt, until at least one stopping event occurs.

In some implementations of the troubleshooting system, the one or more patient specific factors includes a patient current status. The medical device further comprises one or more detectors that may detect the patient current status. The troubleshooting session may further include selecting one or more output modality and/or one or more output characteristics of the selected user prompts based on the patient current status. Furthermore, one or more output modality and/or one or more output characteristics of the selected user prompts may be selected based on the patient current status. In some sessions, a first stored sequence of user prompts associated with a same or similar operational problem may be selected based, at least in part, on the patient current status. A user prompt from the stored sequence may also be selected. A second stored sequence of user prompts or a different next user prompt may be dynamically reselecting based, at least in part, a change in the patient current.

In some implementations of the system, the troubleshooting session may further include selecting a sequence of user prompts from a stored sequence of user prompts based at least in part, on the one or more patient specific factors, wherein the stored sequence of user prompts is outputted from an artificial intelligence model trained, at least in part, on global patient experience data. User prompts may be selected based, at least in part, on the selected sequence of user prompts.

The troubleshooting session may also comprise selecting one or more initial user prompts of the user prompts is further based on one or more prior successful prompts in previous troubleshooting of a same or similar operational problem by the patient.

In some sessions, the stopping event includes determining that the operational problem is resolved, a predefined time for the troubleshooting session is reached, or a threshold number of user prompts are outputted without resolution of the operational problem. A threshold number of prompts maybe outputted without resolution, resulting in contacting of an external support or instructing the user to contact the external support.

A method may be provided for troubleshooting a wearable medical device for a patient in which electrocardiogram (ECG) signals, if available, is received from one or more electrodes coupled to a wearable article of the medical device. The ECG signals may be assessed to detect an operational problem of one or more components of the medical device or determining that no ECG signals are received may also lead to detection of the operational problem. Detection of the operational problem may result in initiating of a troubleshooting session during which one or more patient specific factors are received. A stored sequence of user prompts in plain language and associated with a same or similar operational problem may be selected based, at least in part, the one or more patient specific factors. User prompts are also selected from the stored sequence of user prompts to assist a user in resolving the operational problem. A next user prompt after an initial user prompt is different than prior user prompts in the troubleshooting session. The selected user prompt is outputted via a selected output modality. Steps of assessing of the ECG signals or the determining no ECG signals received, and outputting of the selected next user prompt are iteratively repeated until at least one stopping event occurs In some implementations of the method, at least one of the user prompts may include instructions for the user to manipulate the wearable article or at least one of the one or more electrodes. The one or more patient specific factors may also include a patient current status, and after a first iteration, a different stored sequence of user prompts or a different next user prompt may be dynamically reselected based, at least in part, on a change in the patient current status.

In some implementations, the method may also include applying an artificial intelligence model trained, at least in part, on global patient experience data, to output sequences of user prompts associated with various operational problems. The outputted sequence of user prompts is stored and a sequence of user prompts are selected from the stored sequence of user prompts, based at least in part, on the one or more patient specific factors based, at least in part, on the selected sequence of user prompts.

A method may also be provided in which an assessment is performed to detect an operational problem of the medical device and in response, a troubleshooting session is initiated. Patient specific historical data that relates to the patient may be accessed to determine at least one key prompt, which in previous troubleshooting sessions resulted in resolution of a same or similar operational problem by the patient. The key prompt(s) are outputted and iterative steps are performed in which assessment of the operational problem and selecting of any next key prompt is performed. The selected next key prompt is outputted and the process repeats until at least one stopping event occurs. If the operational problem persists, a next user prompt in a sequence of user prompts is selected and outputted until the stopping event occurs. A troubleshooting system may perform these steps with one or more processors of a computing device.

A method may also be provided for generating a sequence of user prompts to troubleshoot a medical device used by a patient. The method may employ a prompt construct AI model that receives a description of a potential operational problem of the medical device as input as well as potential patient characteristics. The prompt construct AI model performs predictive analysis to predict a sequence of user prompts, in which each user prompt provides a different instruction for a user to individually resolve the operational problem while the medical device is in use, based at least in part, on potential patient characteristics as input to the prompt construct AI model. The sequence of user prompts is generated based, at least in part, on an output result and stored.

This summary is not intended to identify key features of the claimed subject matter, nor is it intended to be used as an aid in determining the scope of the claimed subject matter.

BRIEF DESCRIPTION OF THE DRAWINGS

Various implementations in accordance with the present disclosure will be described with reference to the drawings.

FIGS. 6A and 6B are flowcharts of example methods using a prompt construct AI model, in which FIG. 6A shows an example of employing the prompt construct AI model and FIG. 6B shows training the prompt construct AI model, in accordance with some implementations.

DETAILED DESCRIPTION

Figure 1:
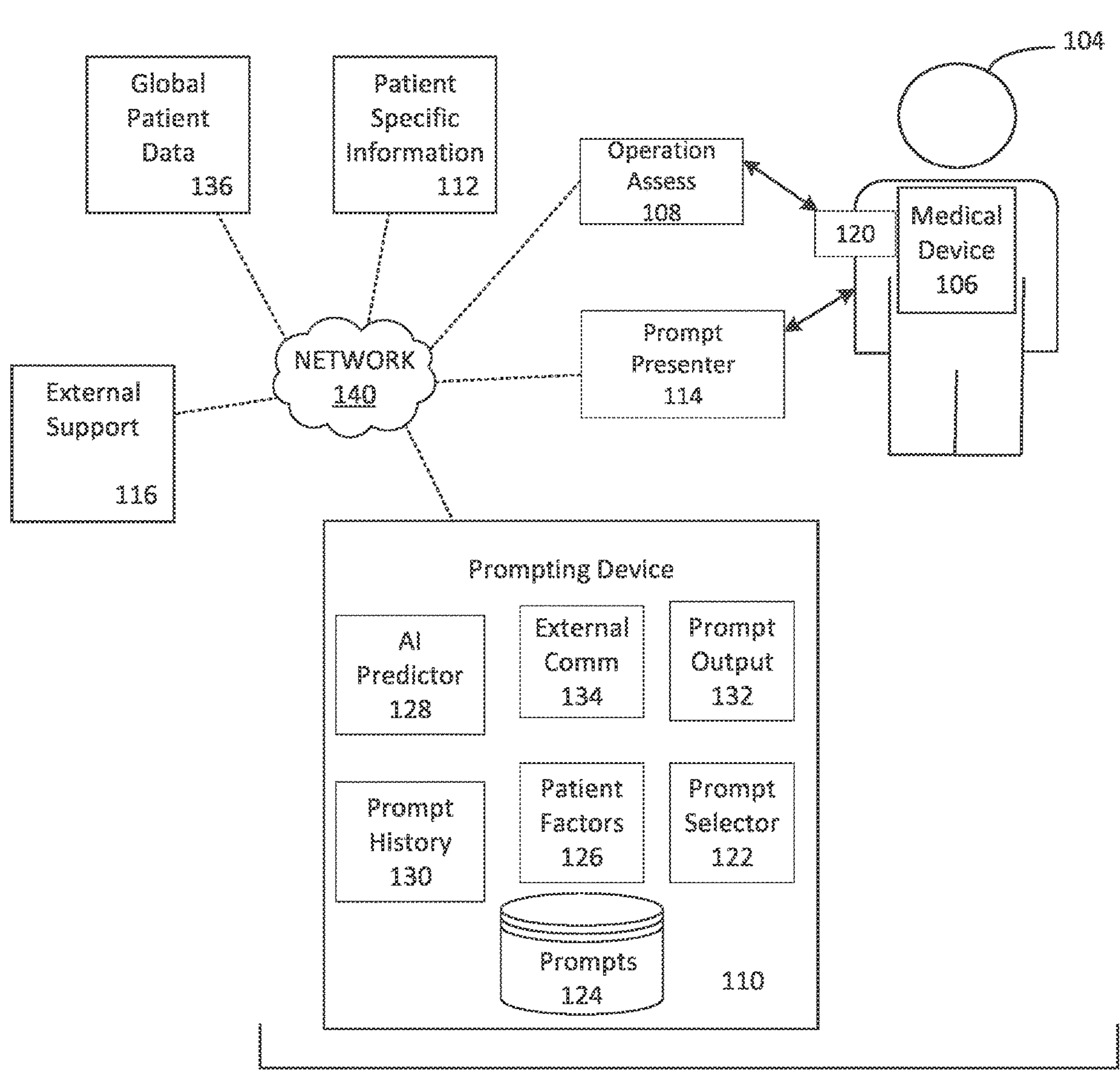
FIG. 1 is a block diagram illustrating an example environment in which various aspects of the medical device troubleshooting system can be implemented, in accordance with some implementations.

In the following description, various implementations are described. For purposes of explanation, specific configurations and details are set forth in order to provide a thorough understanding of the implementations. However, it will also be apparent to one skilled in the art that the implementations may be practiced without the specific details. Well-known features may be omitted or simplified without obscuring the implementations described. The description of the medical device troubleshooting system provides a framework which can be tailored to individual systems built around the medical device troubleshooting system. Elements may be described in terms of "basic functionality" or varying degrees of functionality.

The present medical device troubleshooting system ("troubleshooting system" or "system") provides for ease of use and effective troubleshooting of a problem with the operation of a medical device being used, e.g., worn, by a patient. While in a troubleshooting mode a troubleshooting session is commenced and the system outputs a series of different tailored prompts for a user to follow and rectify the glitch. Rather than repeat a same instruction to a user, the present troubleshooting system presents, in an adaptive manner, different user prompts (also referred to as prompts). A sequence of user prompts may be dynamically selected during a troubleshooting session based on user responsive actions or changes to circumstances, such as detection of changes to identified operational problems, environment, patient current status, etc.

Each user prompt selected from a stored sequence of user prompts is formulated to individually resolve the operational problem, such that a user following any given prompt in the sequence independent of other user prompts, may resolve the identified operational problem of the medical device. Such individually addressable prompts are in contrast with other types of prompting systems in which each user prompt of a sequence is a step that is dependent on other prompt steps leading to a final resolution. User prompts according to the present troubleshooting system, may be presented in various orders or presented according to a path specified by a data structure that stores the sequence of user prompts.

User prompts are different than other user prompts in a sequence according to the presentation of an individual prompt. In some implementations, user prompts may differ in the plain language of the instruction or apply different modalities to present instructions, For example, two or more user prompts in a sequence of user prompts may increase detail of a troubleshooting approach, apply different approaches to address a same problem, or modify the instructions directed to an approach in subsequent user prompts. Some user prompts may be presented using different modalities, such as a user prompt in text, video, images, and motion. At times the user prompt may include a combination of the various modalities such as visual text coupled with a video, diagrams, or device motion. Often the user prompt is presented in plain language for a user to comprehend.

In some implementations, the troubleshooting system can present the user prompts in a manner that accommodates various patient idiosyncrasies. The medical device often includes a wearable device, which can be for extended continuous use or intermittent use. One or more sensors, which may include transducers in some implementations, can detect an operational problem with the medical device. The sensors may detect if the problem is resolved and, at times, generate signals that may be interpreted to automatically trigger a troubleshooting mode to begin a troubleshooting session. The troubleshooting mode may be activated upon such detection or other triggers, such as user activation of a troubleshooting session.

The operational problem may be detected when an aspect of the medical device that is needed for patient care fails to function. The operational problem of the medical device can also include functional issues where the medical device is currently operating at a level of operation below a standard level (e.g., expected performance to provide adequate monitoring or other care of the patient). Examples of operational problems may include too much noise, "leads-off" for one or more electrodes, not detecting a clear rhythm, low power, etc. The operational problems may be identified by other mechanisms, such as user input. Operational problems may be associated with an identifier or description of the operational problem.

In some instances, the operational problem that may be addressed by the troubleshooting system includes potential functional issues, such as when the medical device is found to operate at a standard level, but an aspect of the medical device or patient is predicted to likely result in a future malfunction of the medical device. For example, a potential malfunction may be determined if a component of the medical device decreases in performance level to near a minimum standard level of operation. In this approach, the troubleshooting system functions in a preventive capacity to attempt to ward off future malfunction of the medical device.

Patients and other users respond differently to instructions and have different proficiencies in performing troubleshooting steps. Patients may have different tolerances for accepting instructions presented in various ways, which can negatively affect care of the patient. For example, where the patient becomes annoyed or frustrated with the troubleshooting prompts, the patient may not wear the device as proscribed and added stress may worsen health concerns.

The present troubleshooting system may balance a need to quickly resolve equipment problems with keeping the patient comfortable with using the medical device. In a troubleshooting mode, prompts with different instructions are sequentially presented to a user, so as not to overwhelm the patient with a list of involved troubleshooting items. If a patient is confused about how to resolve a situation, it might not be helpful to repeat the same words over and over. In some situations, attempts by other systems may repeat a same prompt and amplifying the volume with repetitions. Such other approaches may not help the patient understand or resolve the issue and may have negative effects on the patient wellbeing.

Patient specific data may be accessed and utilized to customize user prompts. The patient specific data may include patient demographics, patient medical conditions, patient temperaments (detected in real time or according to stored patient records), patient perception abilities/sensitivities (e.g., sensory, cognitive, or behavioral issues including vision or hearing impairments,), physical movement abilities, patient current statuses (detected in real time), and other information or qualities specific to the current patient that may impact the patient receiving and/or responding to the user prompts.

According to the present troubleshooting system, user prompts are selected to be convenient and intuitive for the user. The troubleshooting system may be customized to a patient by using patient specific information and tailoring prompting to meet the needs of a particular patient, such as in selection of user prompts, adding personalization to a prompt, choosing a tone to present the prompts, specifying a particular output modality, use of timing and frequency of prompts, request for user interactions between prompts, etc. The prompting may be dynamic to change to different prompting sequences by reselecting a new stored sequence of user prompts or a new path in a sequence of user prompts, during a troubleshooting session in response to user/patient responses to the presented prompts. Thus, the user prompts may be adapted on the fly.

Individual prompts may be different from previous prompts during the troubleshooting session. For example, the prompts may ask that a user take different actions with different information presented in various prompts. Different prompts may include instructions for a same user action but include different phrasing or use of words. In some implementations, one prompt may reference a specific component of the medical device and another prompt may include a reference to a different component of the medical device. Between presentation of individual prompts, the medical device may perform a check of whether the problem was resolves, such as with the use of a sensor or requesting user input.

When an operational problem is determined to have been resolved or if a certain number of prompts have been provided without resolution of the problem, the troubleshooting mode is deactivated and the troubleshooting session is ended. In some implementations, the troubleshooting system may store a key prompt that was presented last, before the problem was resolved. If the same or similar problem arises again in the future, the system may immediately default to the key prompt. If the problem persists, the troubleshooting system may automatically contact an external support resource or prompt the user to contact the external resource to help rectify the problem. For example, a service technician may be notified and sent to the patient or the patient may need to bring the device to a technician. The external support resource may determine, for example, that a component may need to be replaced, additional patient training on use may be required, or other solutions.

Other benefits and features of the troubleshooting system will be apparent from the further description of the system and methods, as described below.

The medical devices that may be employed in the troubleshooting system may monitor and/or treat a variety of health concerns, including but not limited to, cardiac function, respiratory function (e.g., chronic obstructive pulmonary disease, asthma), blood glucose levels (e.g., diabetes types 1 and 2), fetal and neonatal status, body temperature, cancer treatment parameters, neurological disorders (e.g., dyskinetic symptoms and tremors), etc.

In some implementations, the medical device employed in the troubleshooting system may include a wearable article. Some simple wearables, for instance smartwatches, can detect basic physiological parameters. Medical-grade monitoring devices generally provide more comprehensive and reliable detection for particular health conditions, such as cardiac conditions.

Extended wear or variations thereof refers to prolonged continuous use of a wearable medical article by a patient. The length of time may be over two weeks. The term "continuous use" or variations thereof, is understood to include daytime use, which may be from several hours of the day and/or at night, to full daytime hours and full nighttime use. In some implementations, the monitoring system may be worn without stop except for temporary daytime removal during brief activities that may expose the monitoring system to potentially adverse conditions, such as water contact, e.g., bathing or swimming, cleaning of the support structure, etc. Thus, "continuous use" is intended to include such brief periods of non-use.

The particular context of these and other related terms within this description should be interpreted accordingly.

FIG. 1 shows an overview of an example environment 100 in which various aspects of the medical device troubleshooting system 102 can be implemented. The troubleshooting system 102 employs a medical device 106 to treat and/or monitor the health of a patient 104, an operation assessment component 108 to check the medical device 106, and a prompting component 110 to output troubleshooting prompts. The prompting device 110 may be included in a dedicated assistant device for the medical device 106, a main electronic module of the medical device (as in 216 in FIG. 2), one or more software programs running on a mobile device, one or more applications on one or more cloud servers, etc.

A prompt presenter 114 may be a component of the medical device 106 such as the prompting component 110, or a separate device that communicates with the prompting component 110. In some implementations, the troubleshooting system 102 may also include or communicate with one or more patient specific data storage resource 112. Various components of the troubleshooting system 102 and/or external resources, such as one or more external support resource(s) 116, communicate with each other via one or more networks 140.

The patient 104, for purposes of this description may also be referred to as a person, is treated and/or monitored by the medical device. The patient 104 can be ambulatory, such that while wearing the wearable article of the medical device 106, the patient 104 can walk around and is not necessarily bed ridden. The patient 104 may also be able to move from place to place with the assistance of another person or use of a mobility device, such as a walker, a cane, crutches, a scooter, a wheelchair, etc.

While the patient 104 may be considered a "user" of the troubleshooting system, this is not a requirement. A user may also be a clinician such as a doctor, nurse, emergency medical technician (EMT), a residential caregiver, acquaintance or relative of the patient, or other similarly tasked individual or group of individuals. In some cases, a user may even be a bystander. The particular context of these and other related terms within this description should be interpreted accordingly.

The medical device 106 may collect health data from the patient 104 and/or treat the patient 104. The medical device 106 may include a wearable article that is worn by the patient 104. An example of the medical device and wearable article is shown below with regards to FIG. 2. Other examples of medical devices and functional components of medical devices that may be implemented with the troubleshooting system, are described in U.S. Pat. No. 9,757,581, filed Apr. 29, 2016, the contents of which are incorporated by reference.

A sensor 120 may continuously or periodically monitor the operation of the medical device. The sensor 120 may be coupled to the medical device 106 to directly monitor operation of medical device components and provide signals to the operation assessment component 108 of the troubleshooting system. Such signals may directly reflect the operational status of the medical device through a self-check, such as a power sensor to signify a present storage level of a power source, e.g., battery.

Some configurations of operational assessment component 108 may use intelligence to determine if an operational problem is present, such as by reference to data stored in the patient specific data resource 112 and/or detected patient specific status. For example, if a patient is in motion, the signals may be different than when the patient is stationary. At times, the operational problem may be caused by some interaction of patient with the medical device. However, non-patient interaction problems may also be detected, such as lower power or lack of data connectivity of one or more of the medical device components, such as an assistant device, server problems, network failure, etc.

In some implementations, the sensor may provide signals that indirectly indicate performance of the medical device, for example, by providing health monitoring signals from the patient. The sensor 120 may include one or a plurality of sensors in contact, or in close association with the patient. Such indirect sensors may detect physiological parameters associated with the health of the patient and generate signals reflective of sensed patient parameters. The patient health signals may be received by the operation assessment component 108 to assess the signals as indicative of the medical device operation. This medical device operation assessment may be different from another assessment of the signals to determine health of the patient. The operation assessment component may compare the patient health signals to signals expected from properly operating sensors. If the patient health signals are outside a normal operating range, the assessment component may determine that the operational status of the medical device is compromised. For example, if no signals are received from one or more of the sensors, an operational problem may be detected.

When the operation assessment component 108 determines the presence of an operational problem, including a potential imminent functional issue with the medical device, a troubleshooting mode may be activated. In a troubleshooting session, a prompt selector 122 of the prompting component 110 may select from stored prompts in prompt data store 124 by considering the identified operational problem and one or more patient specific factors.

Patient factor component 126 may access or receive patient information that is stored by the patient specific data resource 112 and/or provided directly from the medical device in real time. Particular data stored in the patient specific data resource 112 may be accessed with prior consent of the patient 104 (or legal guardian of the patient 104). Although patient specific factors may be used to tailor prompts for a patient user to follow, some patient tailored prompts may also be useful for other users located at the patient's side to attempt to troubleshoot the medical device.

The patient specific factors may be used to select one or multiple output modalities for prompts, such as voice, text, pictures, video, vibration or other device movement. The patient specific factors may also be used to select output characteristics for prompts, such as volume, tone, text size or font, display brightness, white on black text, display colors, frequency of outputting the prompts, prompt language and other output characteristics. For example, patient specific data may indicate that a user prefers a particular language and the prompt may be outputted in that language, such as English, Spanish, American Sign Language, etc. The output characteristics may be dynamically changed on the fly such as in response to a user action in following a prior user prompt in the sequence of user prompts, if a patient current status is detected to change during the troubleshooting session, etc.

In some implementations, the patient factor component 126 may determine from the patient specific factors that a caretaker or other assistant person at the location of the patient may assist in the troubleshooting process. For example, a caretaker may be scheduled to tend to the patient during specific days and/or times and it is further determined that the troubleshooting mode is activated during the scheduled assistant time. In these cases, prompts may be selected to present to the assistant person instead of, or in addition to, the patient. For example, the prompt output 132 may send prompts simultaneously to two or more types of modalities or two or more prompt presenter devices 114 to direct the prompts to both to the patient and assistant person.

Patient specific factors may also include current patient status that is detected by the medical device, inputted by the patient or other user, or other mechanisms to realize a current status. The patient current status may include in-progress actions of the patient, or present state of a patient detected in real time. Patient current status may include at sleep, walking, sitting, exercising, bathing, washing the medical device, driving a vehicle, a detected emotional state of the patient such as under stress, body position, the patient experiencing a medical condition event, etc. Troubleshooting prompts may be different for operational problems occurring during a particular current patient status.

Various detectors of the medical device may be interpreted by the troubleshooting system to determine patient current status. The detectors of the medical device may sense patient physiological parameters (heart rate, breathing characteristics, blood oxygenation, body temperature, etc.), which may be interpreted to determine patient current status. For example, sleeping may be determined using detectors that detect patient respiration (such as ECG electrodes), patient cardiac activity, patient body position, body orientation (such as a 3-axis accelerometer, an example of which is described in U.S. Pat. No. 11,083,906, filed Jan. 5, 2018, the contents of which are incorporated by reference), body movement (such as an accelerometer), body temperature, and/or time of day. Detectors may also indicate body angle and orientation, such as sleeping on the patient back or front. Detector data may be analyzed, such as by the medical device, to determine the patient current status, for example as described in U.S. patent application Ser. No. 17/902,508, filed Sep. 2, 2022, the contents of which is incorporated by reference.

In some situations, a current patient status may indicate a potential future operational problem and the troubleshooting mode may be activated and appropriate prompts selected to avoid such problems. Such potential future or imminent operational problems are considered as under the umbrella of operational problems addressed by the troubleshooting system. For example, for a patient detected to be in motion of a significant level that may lead to operational problems, an order of the prompts may be adjusted in anticipation of the problems a patient may encounter during motion. For example, "Tighten your garment" may be given as the first prompt since this is particularly important during motion. The troubleshooting system may request the user input a response as to whether the prompted action is taken and continue to a next user prompt if an affirmative response is not received. The troubleshooting system may continue to monitor for the potential occurrence of a malfunction.

Some implementations of the troubleshooting system 102 may include an AI predictor model 128 to generate prompts and arrange the prompts into sequences to address various operational problems. The AI model is trained with global patient data from the global patient data resource 136, which may include global patient experience data (related to historical experiences of various prior patients in using the same or similar type of medical device) and global patient specific data (related to characteristics of prior patients who had previously used the same or similar type of medical device) from previous patients. Output results may include prompt sequences that may be stored and applied for various patients. In some implementations, the AI model maybe also trained with patient specific experience data for the subject patient using the medical device and the output result may predict a prompt sequence tailored for the particular patient. Where retraining or updated training of the AI model results in changed output of prompt sequences, the stored prompt sequences may be also updated. Such update may be pushed to or pulled by the troubleshooting system.

Prompts data store 124 can include any electronic data structure, such as a database, to store prompts used by the prompting component 110 in executing various functions to select and present prompts to a user. The data structure facilitates selection and access of stored prompts by the prompting component 110. In some implementations, the data structure may include references to stored prompts, rather than the prompts being stored in the data structure. In these implementations, the data structure references may be used to build a sequence of user prompts.

In some implementations, the prompt sequences stored in the prompt data store 124 may be dynamically updated as new information is acquired regarding use of prompts. For example, newly acquired global patient data, such as updates to the global patient data resource 136 may allow for retraining an AI model to output improved prompt sequences. Also, feedback information received from a user and/or external support resource, e.g., customer service, input or surveys may increase the body of information to improve prompts.

The prompts may be organized in a various data structures, such as a hierarchical decision tree data structure. In some implementations, the prompt selector 122 may determine a starting point in the tree to begin prompting. For example, if the prompt history 130 includes data that the patient had previously been successful at resolving a similar operational problem with a key prompt, the prompt selector 122 may initiate the sequence of user prompts at the key prompt rather than repeat the previously unsuccessful prompts. Should the key prompt be unsuccessful, the prompt selector may choose to continue down the decision tree from the key prompt, may choose to start at the beginning of the decision tree, skipping the key prompt in the decision tree, or chose some other path.

The prompt output 128 communicates with a prompt presenter device 114 to provide selected prompts for presentation to the user. Various prompt presenter devices may be employed to provide various modalities of prompts, as described in detail below with regards to FIG. 2. In some approaches, the prompt presenter 114 may be software running on the prompting device 110 or another local device, such as an assistant device, at or near the patient and communicatively coupled to the medical device 106. In some implementations, the prompt presenter device may be carried by the patient, such as by a carry pack worn or held by the patient.

The prompt presenter 114 may include a hand held user device, such as a dedicated assistant device for the medical device, a mobile device, e.g., a smart phone, tablet or other personal device, that may be controlled by the user. In some implementations, the prompt output component is a wearable device, such as a smart watch, or integrated with a wearable article of the medical device 106. The prompt presenter 114 may be any smart home hub or other household device with built in voice assistant, motion activation, or visual display, (Amazon Alexa, Google Assistant), television display, other smart device with voice recognition and voice service and/or visual display, such as interactive functionalities in automobiles. The prompt presenter may provide prompts in the modality of text, voice or other audio, pictures, video, motion, etc. Voice prompts may be provide in a particular language or multiple language, for example for multi-lingual users. At times, the prompt presenter may output a visual indicating a location of the medical device related to a user action indicated in the at least one prompt. In some implementations, the prompt presenter device 114 may be integrated with the medical device, such as speakers, a visual display screen, and/or motion actuation.

In some implementations, the stored sequence of user prompts may be modified to address the particular operational problem. For example, instead of generally saying "Check sensors," the troubleshooting system may prompt the patient to check a specific electrode that has lost contact, such as, "Check left front sensor," or "Make sure the left front sensor is touching the skin," or "Your left front sensor is not touching the skin. Have you tried repositioning it?" and "If that did not work, please use some lotion on your skin."

In some implementations, an external communication component 134, such as a customer support interface, may communication information to and/or from an external support resource 116, such as to request assistance to further troubleshoot the medical device or otherwise provide support to the user in proper use of the medical device. The external support resource 116 can include one or more servers implemented in the cloud. In some implementations, the prompting device 110 can interface directly or indirectly using an intermediary device, with the external support resource 116, such as via the external communication component 134, over the communication network 140. For example, the prompting device 110 may prompt the user to contact a customer service representative if unable to resolve the operational problem after a prompting stopping event.

The network 140 may include one or more of types of communication configurations, such as a gateway, one or more WANs (Wide-Area Networks) and/or LANs (Local-Area Networks), which may be wired and/or wireless. In some examples, the network 140 may include the Internet and/or one or more cellular networks, such as for narrow-band data over cellular, among other networks. For example, the network 140 may provide a connection, for example, through a local network to a host computer or to data equipment operated by an Internet Service Provider (ISP). The ISP in turn provides data communication services through the world wide packet data communication network (the "Internet"). For example, the troubleshooting system may communicate through one or more gateways to connect with the Internet.

The network 140 may operate according to one or more communication protocols, such as Bluetooth™, Zigbee, Narrowband Internet of Things (NB IoT), LTE (Long-Term Evolution), CDMA (Code Division Multiple Access), WiMax (Worldwide Interoperability for Microwave Access), WiFi (Wireless Fidelity), WiFi Direct (Wireless Fidelity Direct), EDGE (Enhanced Data rates for GSM (Global System Mobile) Evolution), 3G (Third Generation), 4G (Fourth Generation), HTTP (Hyper-Text Transfer Protocol), TCP (Transmission Control Protocol), SIP (Session Initiation Protocol), device contact based transfer protocols, device movement based pairing protocols, and other communication protocols.

Although the network 140 is shown as a single networks, it should be understood that the network 140 may include multiple, distinct networks that are themselves communicatively linked. The network 140 could take other forms as well.

The depiction in FIG. 1 is not to be construed as limiting components of the medical device troubleshooting system 102 and the troubleshooting system 102 is implemented. The troubleshooting system 102 is can be implemented in different ways with additional or less devices. For example, in some implementations, the various sensors or detectors may be employed.

Figure 2:
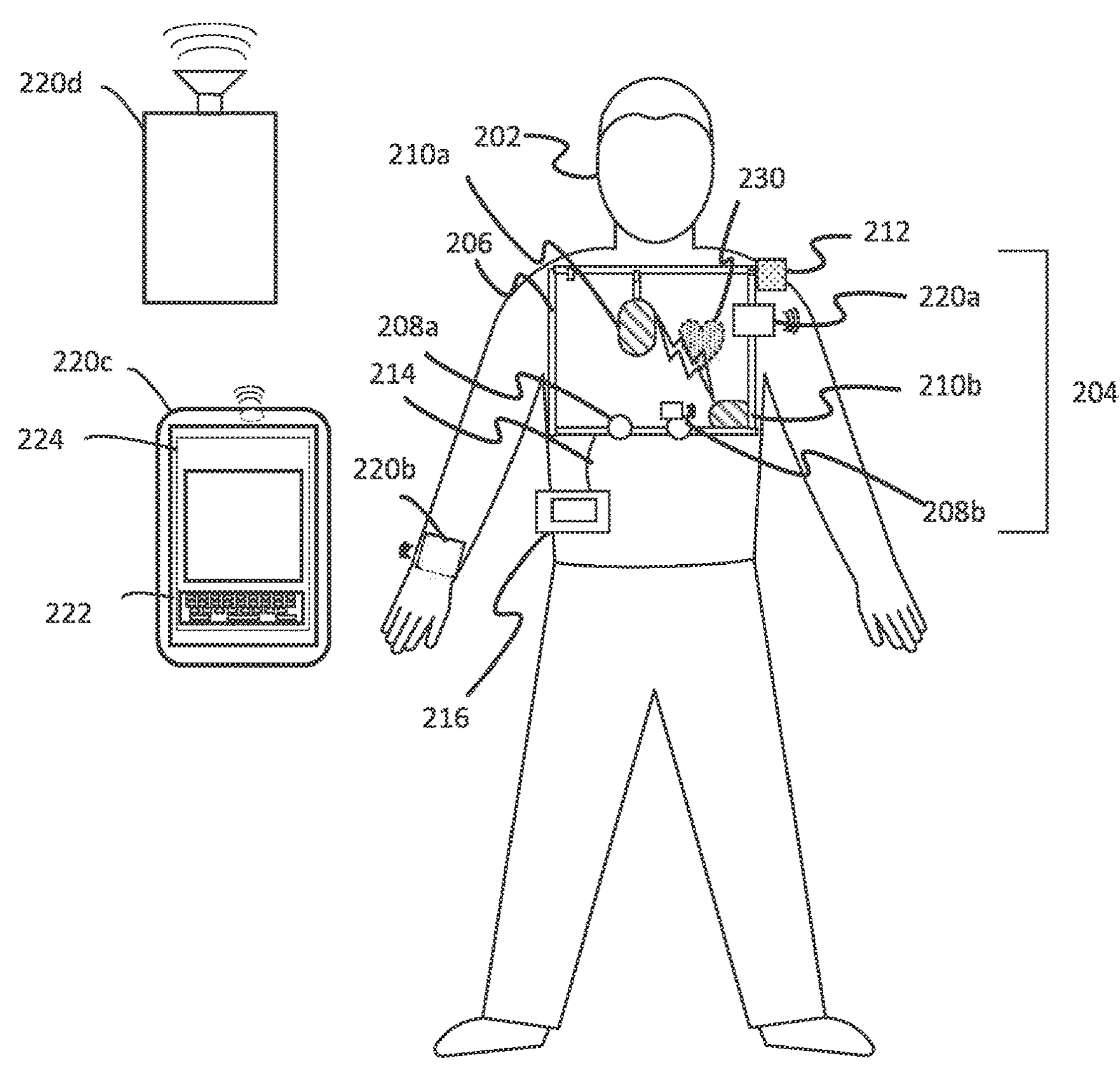
FIG. 2 is a diagram illustrating an example of the medical device troubleshooting system employing a cardiac wearable medical device, in accordance with some implementations.

To illustrate an example of a use case of the medical device troubleshooting system 200, FIG. 2 shows a representative patient 202 with a wearable cardioverter defibrillator system (WCD) 204 (or medical device 204) for continuous wear (e.g., for at least several hours per day, and for at least several days, even a few months) as prescribed by his medical provider. The medical device 204 includes a wearable article 206 (also referred to as a "support structure") worn under clothing and has multiple electrocardiogram (ECG) electrodes 208*a*, 208*b* that are required to have sufficient contact with the skin of the patient at particular locations on his torso in order to accurately monitor the cardiovascular condition of the patient. Defibrillation electrodes 210*a*, 210*b* also require sufficient skin contact of the patient at torso locations to discharge electrical charge. More than two ECG electrodes can be used and distributed around a patient's body. A sensor 212, which may include one or more sensor in an array or a plurality of independent sensors, may be physically coupled to, in communication with, or integrated with the wearable article 206 or other medical device components. Such communication can be implemented by a communication module, as will be deemed applicable by a person skilled in the art in view of this description. The sensor 212 is also described with regards to sensor 120 in FIG. 1.

Some aspects of the external defibrillator include a housing and an energy storage module within the housing. The energy storage module can be housed within the defibrillator and can be configured to store an electrical charge. Other components can cause at least some of the stored electrical charge to be discharged via electrodes 210*a*, 210*b* through the patient, so as to deliver one or more defibrillation shocks through the patient. A lubricant may also be ejected from the medical device at the electrodes for conductive contact.

A main electronic module 216 (e.g., defibrillator) may encase various components of the troubleshooting system 200. For example, in reference to FIG. 1, the main electronic module may include the prompting device 110 or various subcomponents of the prompting device 110, the operation assessment component 108, and/or the prompt presenter 114.

Sensors 212 may include a plurality of electrodes 208*a*, 208*b*, 210*a*, 210*b*, which can be coupled to a processor and/or main electronic module 216 via one or more cables, such as cable 214, such as a therapy cable and/or ECG leads. ECG electrodes 208*a*, 208*b* and/or defibrillation electrodes 210*a*, 210*b* can be configured to be worn by a patient 202 in a number of ways. For instance, electrodes 208*a*, 208*b*, 210*a*, 210*b* can be coupled to the wearable article 206, directly or indirectly. The wearable article 206 can be configured to be worn by a patient 202 so as to maintain electrodes on the body of the patient, often while the patient is moving around, etc. The electrodes can be thus maintained on the body by being attached to the skin of patient, or by being pressed against the skin directly or through garments, etc. In some embodiments the electrode is not necessarily pressed against the skin, but becomes biased that way upon sensing a condition that could merit intervention by the WCD system. In addition, many of the components can be considered coupled to support structure 170 directly, or indirectly via at least one of electrodes 208*a*, 208*b*, 210*a*, 210*b*.

The main electronic module 216 may initiate defibrillation using defibrillation electrodes 210*a*, 210*b*, or hold-off defibrillation, based on a variety of inputs, and/or signal outputs, including the ECG signal obtained using ECG electrodes 208*a*, 208*b*. On an occasion an electrode may not properly adhere to the skin or stay pressed against the patient's body so that good electrical contact can facilitate measurement of clear physiological parameters. With proper amounts of lubricant, proper electrode performance may be detected by a low-impedance connection with the electrode. On such an occasion, an operational problem may be detected and a troubleshooting session may be activated to output a prompt or sequential prompting to the patient/user instructing what to do to correct the electrode-to-skin contact problem. For example, a high impedance that may make the device more prone to noise pickup and a prompt to resolve the issue may be to add lubricant to the electrode.

When electrodes 208*a*, 208*b*, make sufficient electrical contact with the skin of patient 202, in case of a WCD, the WCD can detect a shockable rhythm and administer a brief, strong electric pulse (e.g., shock, defibrillation shock, therapy, electrotherapy, therapy shock) through the body of the patient through defibrillation electrodes 210*a*, 210*b* in attempts to bring back a normal heart rhythm. The electric pulse is intended to go through and restart the heart 230, in an effort to save the life of patient 202. In some instances, the electric pulse can include one or more pacing pulses of lesser magnitude to simply pace the heart 230 if needed.

The wearable article 206 (support structure) can be implemented in many different ways. For example, it can be implemented in a single component or a combination of multiple components. In embodiments, the wearable article 206 could include a vest, a half-vest, a garment, etc. In such embodiments such items can be worn similarly to analogous articles of clothing. In embodiments, the wearable article 206 could include a harness, one or more belts or straps, etc. In such embodiments, such items can be worn by the patient around the torso, hips, over the shoulder, etc. In embodiments, wearable article 206 can include a container or housing, which can even be waterproof In such embodiments, the support structure can be worn by being attached to the patient's body by adhesive material, for example as shown and described in U.S. Pat. No. 8,024,037. The wearable article 206 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples as well.

It will be understood that the wearable article 206 is shown only generically in FIG. 2, and in fact partly conceptually. FIG. 2 is provided merely to illustrate concepts about wearable article 204 and is not to be construed as limiting how the wearable article 204 is implemented, or how it is worn. Detailed examples of various wearable articles and medical devices may be employed.

The medical device 204, according to some implementations, can obtain various additional data from patient 202. For collecting such data, the medical device may optionally include at least sensor 212 that may be positioned outside of the wearable article 206. In some implementations, the sensor 212 could be provided as a standalone device, for example separate from the wearable article 206 or housing of defibrillator. The sensor may also be physically coupled to the wearable article 206. In addition, device 180 may be communicatively coupled with other components that are coupled to wearable article 206. Such communication can be implemented by a communication module, as will be deemed applicable by a person skilled in the art in view of this description.

Sensor 212 can be configured to sense or monitor at least one local parameter, such as a parameter of patient 202, or a parameter of the WCD system, and/or a parameter of the environment. The sensor renders a signal responsive to the sensed parameter. The signal may be interpreted as quantitative data, such as values of a sensed parameter, or qualitative data, such as a comparison of the data to a threshold value. The term "meeting" a threshold, or variations thereof, as used in this description means a value being equal to or exceeding the threshold amount.

In some implementations, the signal is in the form of a qualitative, such as informing whether or not a threshold is met, and so on. Sometimes these inputs about patient 202 are also referred to herein as physiological inputs and patient inputs. In embodiments, a sensor can be construed more broadly, as encompassing many individual sensors.

Returning back to the illustrative use case, the representative patient removes the wearable article component of the medical device to avoid the medical device exposure to water, such as to bath, swim, or to wash the wearable article. The system may recognize a lack of signals and interpret a possible cause of the failure to receive signals. In some implementations, the patient specific information may include a typical daily or weekly patient task schedule, which may include when the patient baths, washes the wearable article, swims, sleeps, drives a vehicle, exercises, eats, disconnects to switch batteries, etc.

Patient current status may be detected by the medical device sensors. If a failure to receive signals is detected during a scheduled time that the sensors are intentionally removed, the troubleshooting system may pause for a waiting period to check if the signals return before activating a troubleshooting session. The troubleshooting system may also determine that the patient has been continuously wearing the wearable article for more than a number of hours with no break in wear time. The system may ask the patient if the wearable article is being taken off to shower or to wash the garment. In other implementations, the troubleshooting system may request that the user enter information that confirms that the sensors were intentionally and temporarily removed. If the user confirms a situation in which signal failure is normal, the troubleshooting session is not activated. Otherwise, if the user fails to confirm, then the troubleshooting session may commence. In this use case scenario, the representative patient 202 uses a keyboard 222 or voice recognition of a smartphone 220*c* and enters input into a user interface 224 to confirm temporary removal of the sensors and also enters an expected return time.

In some implementations, the various types of prompt output devices 220*a*, 220*b*, 220*c*, 220*d* may display visual prompts in a graphical user interface (GUI) 224 for the user to view. In some implementations, the GUI may enable user interaction, such as the user responding to prompt questions displayed on a portion of the GUI by using various user input mechanisms. User inputs may include the keyboard 222 including alphanumeric and other keys to enter text or activate control functions. In some implementations, a user contacts the display screen using a finger or stylus in order to select items displayed by the display screen.

The prompt output device may accept various other inputs, such as, without limitation, audio, e.g. voice recognition, touchscreen, switch input with an on-screen or external keyboard, head mouse, gesture recognition, facial recognition, movement tracker, eye movement tracker, smart buttons, trackball, track pen, pen tablet, pen, stylus, and hand mouse. The input may include a user applying touch, voice, click, tap, type, gestures, movement (e.g. moving an eye, arm, body), and other actions.

When the representative patient is ready at to put back on the medical device, the wearable article is worn on the patient and components of the medical device reattached. In one example instance, the patient 202 fails to reattach one of the electrodes 208*a*, 208*b*, 210*a*, or 210*b* to make sufficient skin contact. An operation assessment component, such as a software program running on the medical device or on a separate device, reads the sensor signals and detects that a sensor fails to detect the electrical heart 230 pulses of the patient. The failure of the sensors triggers a troubleshooting mode to output prompts during a troubleshooting session for the patient to act in rectifying the sensor problem.

The troubleshooting system, can access patient specific information that may be stored away from the medical device. Patient specific factors based on the stored patient specific information may be used in selecting a next user prompt, as described below with regard to FIGS. 4 and/or 5. At times, patient specific factors may be employed to choose an output modality, such as a visual display, audio (voice or sound), and/or tactile stimuli, e.g., vibration patterns, as output of the prompts.

In this particular use case, the troubleshooting system receives patient specific information that the representative patient 202 has a vision impairment. The prompting component, as in 110 in FIG. 1, uses this patient perception factor and determines that the patient may be hindered by his eyesight to read visual prompts such as text or a video. The prompt selector selects an audio modality for the prompts based on the patient vision. The audio prompts may also be accompanied by an output of tactile stimuli, such as vibrations, for example, to alert the patient that an audio prompt is or will be outputted.

In this use case, the accessed patient specific information also includes a diagnosis of high anxiety for the patient. The prompting device may use this patient temperament factor to select a stored sequence of user prompts that are fewer in number than a full sequence of user prompts stored to address a same operational problem. The troubleshooting system may also set a stopping event to occur after a fewer prompts as compared to a typical threshold number of prompts. Of the sequence of user prompts to be used, the prompt selector may select prompts identified as a calming in the wording used and an output characteristic may include audio with a soft and amicable tone.

In some implementations, sequences of prompts may be categorized to be selected for various patient specific factors. For example, particular sequences of prompts may be labeled in terms of complexity or level of detail, such as basic, moderate, or high. Selection of a category of a sequence of user prompts may be consistent with the patient traits, as determined by the patient specific factors.

With the prompts, output modality, and output characteristics selected for the representative patient, the prompt output device presents the prompts. The patient has a variety available prompt output devices, such as an output speaker component 220*a* of the wearable article 206, a smartwatch 220*b*, the mobile phone 220*c*, and smart home hub 220*d*. Other prompt output devices are possible that employ various output modalities. The output device may be a multi-purpose device not dedicated to the troubleshooting system and runs software application(s) to perform certain functions of the troubleshooting system, such as outputting prompts. The prompt output device may be located on a wearable component of the medical device and can include a touch screen, a speaker and/or motion or vibration feature.

The representative patient receives the following sequential voice prompts and attempts to follow each prompt instruction after each prompt is presented. Leads off event prompts may individually and sequentially include, for example:

Are you wearing the medical device? If not, put on the wearable article.

Adjust the Garment so the sensors are flat and touching bare skin.

Check that the Garment is not twisted and there is nothing under it.

Moisten the skin under the sensors with water or lotion.

Tighten the Garment by adjusting the front closure snaps and shoulder straps.

Clean the Hub Receptacle and sensors.

If the problem is not resolved and a stopping event occurs, the prompting device may output a stopping prompt to the patient regarding a leads-off correction for the patient to call customer support.

Figure 3:
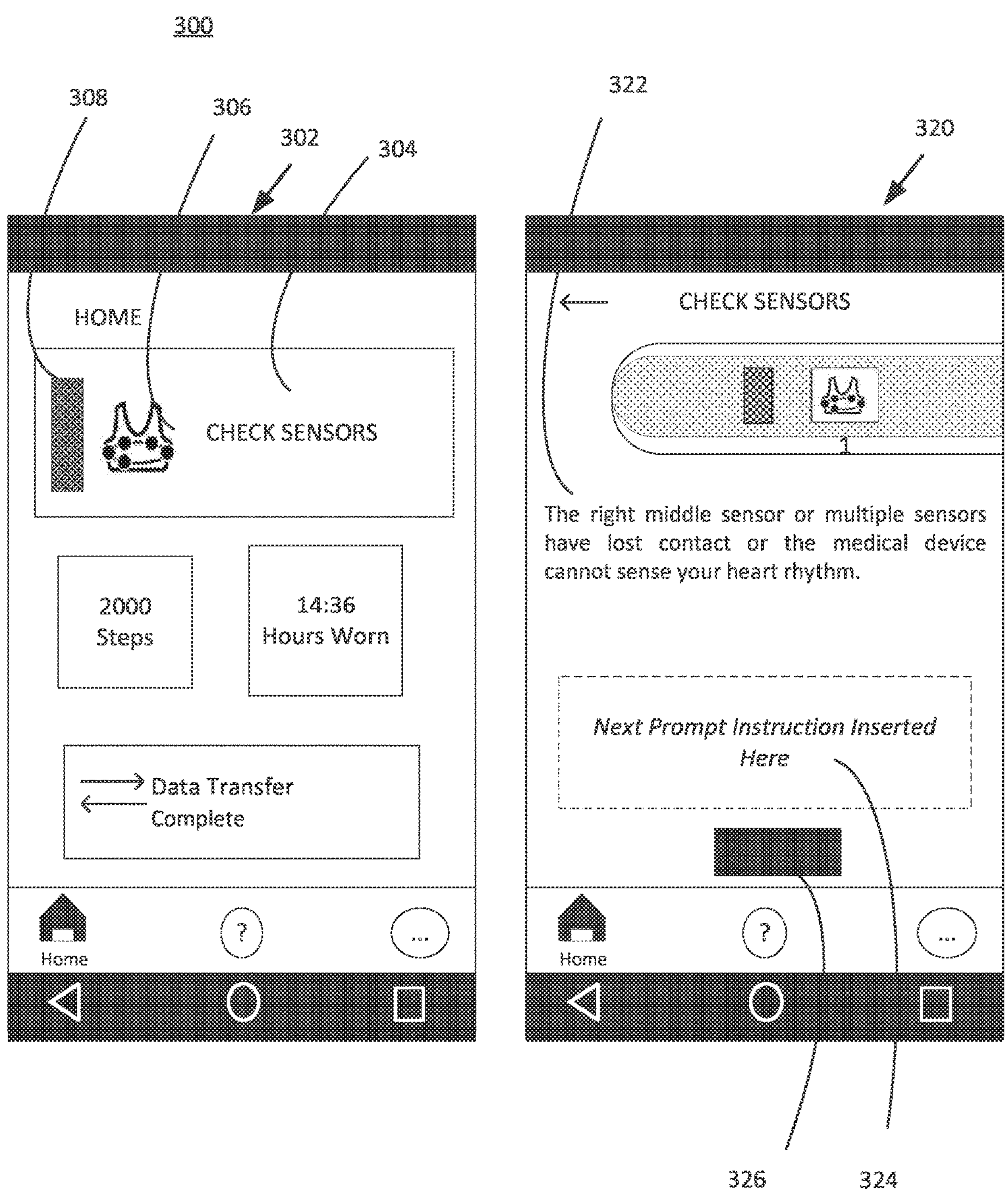
FIG. 3 is a schematic diagram of an example of graphical user interfaces showing sequential troubleshooting user prompts, in accordance with some implementations.

FIG. 3 depicts an example of a display screen 300 showing graphical user interfaces (GUI's) 302 and 320 showing sequential troubleshooting prompts to address a particular medical device problem. Home GUI 302 displays a problem alert 304 with text of a basic identification of the detected problem, graphics 306 indicating the general component of the medical device having problems and a general alert indicator 308.

Troubleshooting prompt GUI 320 displays a detailed text description 322 of the operational problem. For example, the description shown states, "The right middle sensors have lost contact or the medical device cannot sense your heart rhythm." The prompt GUI 320 displays prompts 324 one at a time with time for the user to act in response to each displayed prompt 324. A stop control element 326 may also be provided for the user to manually override the troubleshooting session.

In some implementations, the user interfaces 302 and 320 may be configured for special accessibility accommodations for a patient. For example, a patient may opt to receive an accessibility UI configuration, such as large text or voice description of the user interface.

Figure 4:
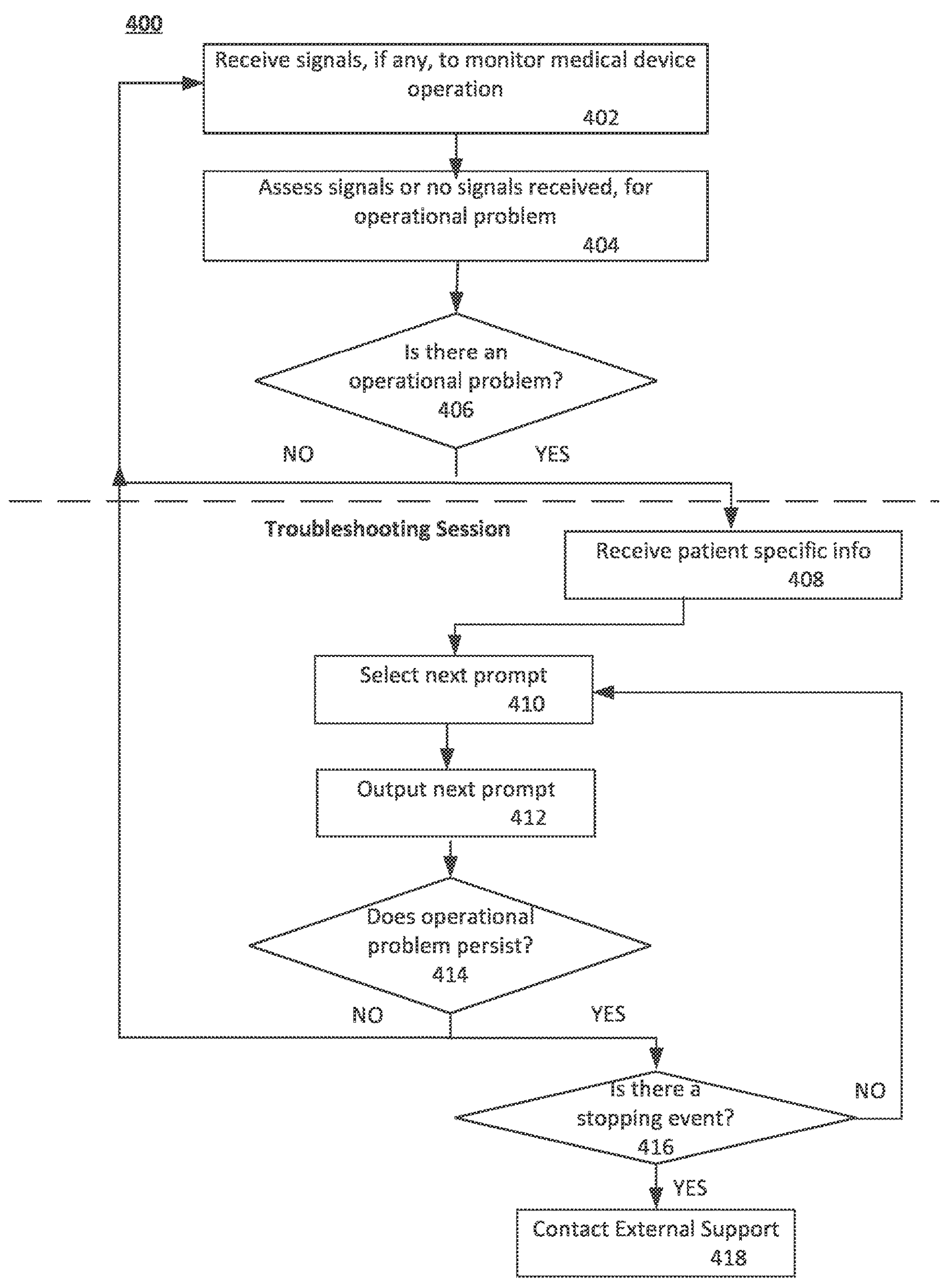
FIG. 4 is a flowchart of an example method for troubleshooting an operational problem, in accordance with some implementations.

FIG. 4 shows a flowchart of an example troubleshooting process 400 performed by the medical device troubleshooting system. One or more aspects of the troubleshooting process 400 may be performed on an assistant device, such as a mobile phone, running a troubleshooting software application to execute the process 400. In some implementations, updates to the prompting sequences, such as through AI model retraining, may be pushed to the assistant device.

In block 402, where signals are available from a sensor, the signals may be received that are indicative of the operational health of the medical device. The signals may be generated by one or more sensors associated with the medical device and/or patient. The signals may be directly indicative of the operational status of components of the medical device by the sensor sensing one or more characteristics of the medical device. The signals may also be indirectly indicative of the medical device operations by intercepting the medical device performance or characteristics of the environment. At times, a sensor that is expected to produce signals may fail to generate the signals.

In some implementations, the signals can be an ECG electrode signal, a pulse oximetry signal, motion signal, or some other type of physiological parameter signal of the patient. The troubleshooting system interprets the physiological patient signals to determine whether they indicate a poorly functioning medical device.

In block 404, the received signals are assessed or it is recognized that there is a failure to receive signals. In some implementations, the signals may be compared to a threshold level for the signals. For example, signals that indicate a power level of the medical device may be compared to an acceptable threshold level of power. For some received signals, a comparison is made with reference signals that are expected from either a properly operating medical device or malfunctioning device. In some implementations, normal operating reference signals may include a range of patterns of signals that may be expected from a healthy patient as well as a patient experiencing various health concerns. In some implementations, baseline signals are stored for a properly operating medical device when in use for a particular patient.

In decision block 406, it is determined whether an operational problem currently exists. In some implementations, it is determined whether the assessment of the signals is indicative of an operational problem. For example, a pattern of signals compared to reference signals in block 404 may be indicate proper operation or poor operation of the medical device component. At times, no signals may be received, automatically signifying an operational problem. In some implementations, other types of assessments may be performed to detect the operational problems of the medical device, rather than or in addition to receiving and assessing the signals in blocks 402 and 406.

In some implementations, baseline physiological parameters of the patient can be measured, such as the heart rate of the patient while resting, motion detector outputs while walking, etc. The measured values of such baseline physiological parameters can be used to customize the troubleshooting system, in order to make its detection and/or decisions more accurate, since patients bodies differ from one another. Such parameter values can be stored in a memory of the troubleshooting system, and so on. Moreover, a programming interface can be made according to implementations, which receives such measured of baseline physiological parameters. Such a programming interface may input automatically in the troubleshooting system these, along with other data.

Where an operational problem of the medical device is determined, a troubleshooting session may be initiated and the process proceeds to block 408 to receive patient specific factor(s). At times, the troubleshooting mode is entered if an operational problem is detected and maintained for a period of time prior to outputting prompts to the user. In some instances, the system may provide one or more alerts to the patient informing of the operational problem. Such alerts may be provided prior to presenting prompts and after a certain number of alerts or an alert time, the troubleshooting mode may start. Alerts are not considered prompts that include instructions on actions to be taken by the user. A predefined number of alerts without resolution of the problem may also cause the troubleshooting system to enter a troubleshooting mode for that problem. The troubleshooting mode may be canceled or overridden by user interaction, such as voicing a stop command or pressing a stop button.

The patient specific factors may include patient current status, such as whether the patient is at sleep, walking, sitting, exercising, bathing, washing the medical device, etc. The prompt sequence may be selected as a signature for patient statuses. The prompting may be paused until an activity is complete, such as a temporary activity that may interfere with sensors including brushing teeth creating periodic motion at a regular frequency. An example of a prompt sequence labeled as “patient in motion” may include the following prompts:

Stop all movement—count to 10 slowly while signal is obtained.

Reduce any motion until you hear—“It’s okay to move now.”

If the patient status that the medical device is intentionally removed by the patient, such as during bathing, the prompts may be selected to assist in putting the medical device back into operation, such as prompts on how to assemble the garment and electronics into the laundered garment.

Other patient specific statuses may be associated with a patient sleeping, resulting in different prompt sequences, modalities or output characteristics. For example, prompting may be suppressed while the patient is sleeping if the operational problem is not deemed critical. In some implementation, sleeping can be detected by the medical device via a lack of patient motion along with a posture that is horizontal and/or time of day. The frequency of patient alerts in general may be reduced while sleeping. Prompting mode(s) requiring user interventions may be provided after the patient wakes up. In a further scenario, output characteristics, such as voice prompt volume could be modified during motion (e.g., louder) or while sleeping (e.g., louder if urgent or softer if not urgent).

In block 410 a next user prompt is selected, which may be a first initial user prompt at the start of the troubleshooting session or subsequent user prompts after an initial user prompt is presented. The prompting selection may be adaptive to how the user responds to a given prompt during the troubleshooting session. For example, if there is detected a long user response time for a particular instruction, the prompting session may provide simpler instructions to provide helpful hints in the next user prompts.

In some configurations, successive prompts in a sequence may increase detail and suggestions provided to the user. For example, an early prompt may state, “Adjust your garment now” and a subsequent prompt may state, “Try to adjust the garment so that the sensors are flat and touching bare skin.” Another subsequent prompt may specify a particular sensor that is failing to operate properly, along with a diagram of the location of the problematic sensor and/or video of how to adjust the garment or other visual clues.

The sequence of user prompts may be selected for distinct events and operational problems. For example, there may be different stored sequences to address putting on a wearable article, for electrode leads-off, for therapy pads off, excessive noise, device electrical connections (hub to monitor), excessive noise, low battery alerts, etc. Each of these troubleshooting modes may provide a separate list of prompts intended to help resolve the particular problem.

In some implementations, selection criteria may be employed in determining a user prompt and/or sequence of user prompts. The user output device that the user uses to output the user prompt may be a selection criteria. A user output device may be incompatible with an output modality of a user prompt and be rejected in prompt selection. For example, a user output device, such as a home hub, may not be associated with a display screen and user prompts that include text, images, and video may not be compatible and user prompts with voice and/or motion are selected.

In block 412, the selected next user prompt is outputted. In some implementations, the prompt may be presented in a multimedia modality, such as a picture to illustrate an area of a wearable article in which a component is not positioned correctly, or how to insert the battery or plug the cable correctly, how to remove the battery, and so on.

In some implementations, the troubleshooting prompts may be interactive. For example, instead of telling the patient to make sure the sensors are flat and touching the skin, the troubleshooting system could ask, “Are the electrodes flat and touching your skin?” The patient could reply verbally or via a user interface (UI) control. If the patient says “No,” then the device may give an appropriate reply such as, “The electrodes must be flat and touch your skin for proper operation.” If the patient says, “Yes” (electrodes touching skin), then the troubleshooting system may output next user prompt to help resolve the situation, like “Hmm, could the garment be twisted? Did you check?” If the answer is “no,” the device can prompt—“Try putting some lotion on your skin.” If the problem persists, the device can say—“Let’s call customer support. Here is the number. Would you like to call now?

In decision block 414, the system checks as to whether the operational problem persists. In some implementations, the troubleshooting system may wait for a response time window, after which, if no input is received, signals may be reassessed to determine if the problem has been resolved. The system may also request user input between prompts, such as checking a box or verbally stating “Yes” or “No.”

If the operational problem is resolved, the troubleshooting session is concluded and the troubleshooting mode is inactivated. When the troubleshooting system concludes that a troubleshooting situation has been corrected, it may provide a confirmation to the user that user action is successful. The confirmation may be provided via a simple tone, chime, or happy sound, or it could be a verbal confirmation (e.g. "Contact detected"), or other confirmation output. The process returns to block 402 to continue monitoring the medical device for future operational problems.

In decision block 416 is it determined whether a stopping event occurs, such as resolution of the operation problem. In some implementations, a stopping event may include the operational problem persisting after cycling through a prompt sequence to the end of the sequence. Other stopping events may be a predefined period of time had been reached, such as a time lapse since identifying the operational problem. Other stopping events may include a threshold number of user prompts that are outputted without resolution of the operational problem. The user may also enter a stopping event by activating a control, such as a button on the prompt presenter user interface. Additional stopping events are possible. If there is not a stopping event, the process returns to block 410 to select a next user prompt.

If a stopping event is detected but the problem persists, the process proceeds to block 418, to contact an external support resource. For example, the troubleshooting system may present a communication control element, such as on the user interface, for the user to call a support representative. In some embodiments, a notification can pop up on the user's mobile device, such as device 150, with an appropriate number and a touchscreen to press or voice activate the call by the user. In some implementations, the troubleshooting mode can be switched off after an extended period of time with fewer than a certain number or no additional detection of operational problems (e.g. an hour with no leads-off events).

If no stopping event is detected after it is found that the operational problem persists, the process returns to block 410 to select a next user prompt. At times, the that the operational problem has changed since a prior user prompt. For instance, where a user attempts to rectify the problem according to a prompt. the operational problem may become partially resolved as a result, such as one of two electrodes initially found to be operating poorly is now functioning properly. In another instance, user action or time to rectify the initial problem may result in additional operational problems of the medical device. In such circumstances, the sequence of user prompts may change to accommodate the changing operational problem(s).

The steps of the troubleshooting process 400 may be performed by components of the medical device troubleshooting system, and may be performed under the control of one or more computer systems configured with executable instructions and/or other data, and may be implemented as executable instructions executing collectively on one or more processors, for example prompting device 110 in combination with prompt presenter 114 with reference to FIG. 1. The process 400 may also be performed as a service of a cloud server. In some implementations, troubleshooting process 400 may include additional steps or less steps, and the steps may be performed in various orders.

Figure 5:
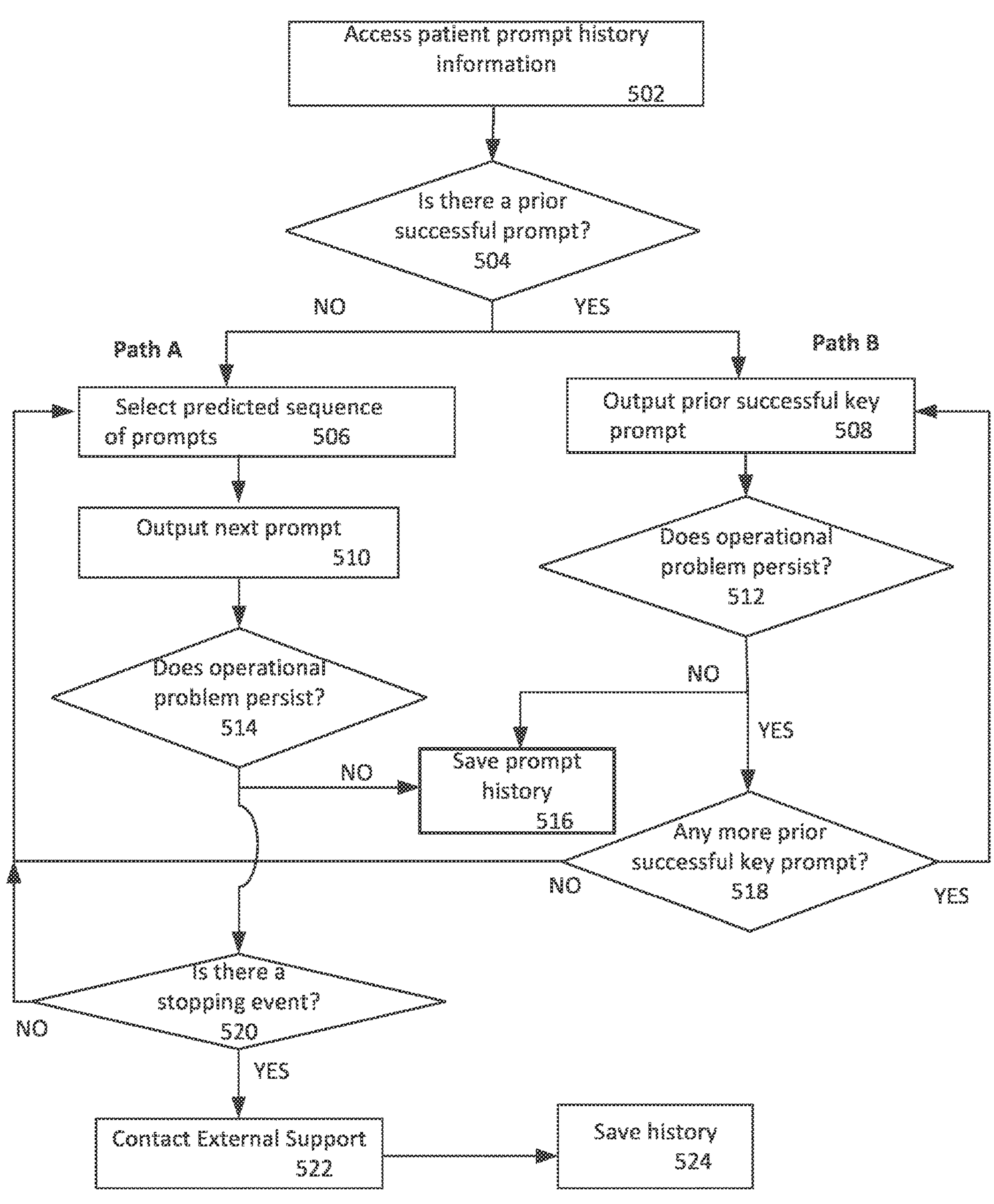
FIG. 5 is a flowchart of an example method for adaptive user prompt selection, in accordance with some implementations.

FIG. 5 shows a flowchart of an example method of selecting prompts to output during a troubleshooting session, which can take into consideration the past operation problems and prompt history. If a same or similar problem occurred in the past, the data of the prompt that aided a resolution of the problem can be retrieved as the priority prompt(s) upon the next occurrence of the problem. Operational problems addressed by the method of selecting prompts may be detected using the steps described above with regard to FIG. 4. Other identification of operational problems are possible, such as notifications of a problem with the medical device manually entered by a patient or other user, A remote computing device that receives data from the medical device, a healthcare provider of the patient, etc.

In block 502 patient specific information is accessed that includes patient history information. The patient history information may include prior operational problems of a same or similar type that the patient experienced with the medical device, or a same/similar type of medical device. The history information may include prior unsuccessful prompts that failed to lead to problem resolution, as well as information on output modalities and output characteristics, such as volume of an audio prompt. The history information may further include prior troubleshooting prompts that were successful at resolving specific operational problems.

In decision block 504 it is determined whether there are any prior successful prompts ("key user prompt" or "key prompt") in the patient prompt history. A user prompt may be identified as successful when the user prompt is the last one outputted prior to detecting the operational problem is resolved.

Past operational problems referenced may be of the same type (e.g., same sensor dislodged) or similar type (e.g., a sensor is dislodged but not the same sensor as before) as the subject problem being currently addressed. If there are no prior successful prompts, the process proceeds down a flow path A to select a sequence of user prompts in block 506 for the patient. If there is one or more stored prior user prompts for the patient, the process proceeds down a flow path B to present one of the successful prompts to the user in block 508.

The prompts may be stored in various data structures having a sequence of user prompts. Data structures may include non-linear structure such as a hierarchical decision tree with prompts as nodes or a graph. The data structure may also be a linear static structure or linear dynamic structure such as an array, a linked list, stack, table, etc. In some implementations, the prompts are arranged in an ordered list or chain of prompts. Other storage data structures are possible.

Stored data prompt sequences may be labeled or otherwise organized to address particular operational problems, or categories of operational problems. The prompt sequences may also be labeled according to one or more patient specific factors, such as specific current patient statuses. In some implementations, different combinations of prompt sequences may be employed, such as patient-in-motion prompts along with normal patient status prompts. Sets of prompt sequences may be associated with different weights to be considered when choosing an order to present the set of prompts. For example, in-motion prompts may be presented prior to normal patient status prompts.

In block 506, the selection of a sequence of user prompts may be using a prompt selection AI model to predict a prompt sequence likely to best facilitate the particular patient to resolve the issue. However, selection of the sequence of user prompts in block 506 need not use the prompt selection AI model, where selection is performed by other software program(s). Selection of a next user prompt can be based, at least in part, patient specific factors for the patient, such as patient current status detected by the medical device or otherwise determined, such as entered by the user into the system. In some cases, a output modality and/or output characteristic of the selected user prompts may also be determined based on the patient specific factors, such patient current status.

Sequences of stored prompts in a data structure are accessed, such as by the prompt selection AI model or other prompt selection program. In some implementations, rather than beginning the prompt output at the top of the prompt data structure, the prompt selection AI model may select a particular prompt at any point of the sequence of user prompts to begin the outputting. For example, if a particular prompt is a node partially down a tree and that prompt is deemed to be highly likely to result in rectifying the operational problem, the outputting sequence may begin at that starting point while ignoring the prompts at nodes farther up the tree.

In some implementations, the prompt selection AI model may be trained with global patient experience data in which other patients using the medical device encountered a same or similar operational problem. Similar operation problems may be characterized in that a particular troubleshooting prompt sequence may be applied to different operational problems.

In some implementations, the prompt selection AI model may further predict an output modality and/or output characteristics that is/are likely to best facilitate the particular patient to resolve the issue. In some implementations, the troubleshooting system may learn a pattern of events of the patient and adjust the prompts and/or prompt timing characteristics accordingly. If the similar or same type of operational problem generally resolve itself, then it may not be necessary to give as many prompts. If multiple prompts have been given and the situation has not resolved, then the troubleshooting system may choose to decrease the frequency or threshold number of the prompts and activate a stopping event to end the troubleshooting session earlier than typical troubleshooting sessions for the general patient population, since the past prompts have been shown to not be helpful for a particular patient.

In some implementations, the prompt selection AI model may be employed to evolve the sequence of user prompts for a particular patient based on patient prompt history including a record of what resolved the issue vs the prompts that the patient did not find helpful.

Once the sequence of user prompts is selected, in block 510, a next user prompt is outputted according to the prompt selection AI model prediction(s). Each of the next user prompts are different than prior user prompts already presented in the troubleshooting session. In block 514, it is determined whether the operational problem persists after the user acts according to the last outputted prompt. If the problem is resolved, the prompts and information from the troubleshooting session is stored in block 516 for future reference and/or updating AI model training datasets.

If the operational problem is not found to have been resolved in block 514, the process may determine if there is an occurrence of a stopping event in decision block 520, as described above with regard to block 416 in FIG. 4. If there is a stopping event, an external support may be contacted, as described above with regard to block 418 in FIG. 4. In block 524, the troubleshooting session is saved in block 524 as historical information, described above in block 516.

Where the troubleshooting session proceeds down path B to use historical successful prompts in block 508 prior successful prompts are prioritized. Prioritizing past prompts may avoid reduce troubleshooting time and burdening the patient with going through a full troubleshooting prompt cycle or decision tree. If a similar problem occurred in the past, the prompt selector can retrieve the last prompt(s) used after which the problem no longer persisted according to the stored history, and output that prompt as the first prompt(s).

When a prompt presented in previous attempts to rectify a same or similar operational problem for this patient is successful in resolving the problem, In some implementations, prompts that rely on previous successful prompts may be modified to remind the user of previous successful actions. For example, a prompt may state, “You may recall, we have done this in the past. Remember the last time you applied a little lotion to the skin and it resolved? Can you try it again?”

In decision block 512 it is determined whether the operational problem persists after each output of a prior successful prompt. Where the prior user prompt is successful again during the present troubleshooting session, the prompt sequence associated with the particular operational problem is stored in block 516. Storage may also include other information relevant to a troubleshooting session such as the prompt modality, prompt output characteristics, relevant patient specific information, user response time, etc. for the troubleshooting session.

In block 518, in cases that a problem persists after outputting the prior user prompt, it is determined whether there are additional key prompts that were previously successful for the type of operational problem at hand, or similar types of past operational problems.

In some implementations, there may be more than one key prompts extracted from the patient history. For example, the operational problem may have occurred on more than a single occasion and there may be different user prompts employed by the user that had resulted in overcoming the operational problem. In other implementations, more than one user may have used various user prompts for a same patient, or one user may have used various prompts for different patients, all addressing a same operational problem. In such cases, the a key user prompt may be selected from the group of available key user prompts. Each key prompt is different from prior key prompts presented in the troubleshooting session.

If there are no additional key prompts stored for the patient, the system proceeds down path A to predict a prompt sequence to follow in block 506. The process continues as described for path A above.

If a next user prompt after the key prompt(s) is/are unsuccessful, the selection process may continue at any point in the sequence of user prompts in block 506. For example, the system may continue selecting next user prompts down a sequence of user prompts from the last key prompt attempted by user during the preset troubleshooting session. In other implementations, after a last key prompt is attempted, the troubleshooting system may continue selecting from the top of the sequence of user prompts and skip the key prompt as a selection if the key prompt is reached. In still other implementations, one or more patient specific factors are employed in the selection of a point to continue in the sequence of user prompts.

The steps of the troubleshooting process 500 may be performed by components of the medical device troubleshooting system and may be performed under the control of one or more computer systems configured with executable instructions and/or other data, and may be implemented as executable instructions executing collectively on one or more processors, for example one or more components shown in FIG. 1. The process 500 may also be performed as a service of a cloud server. In some implementations, troubleshooting process 500 may include additional steps or less steps, and the steps may be performed in various orders.

Figure 6A:
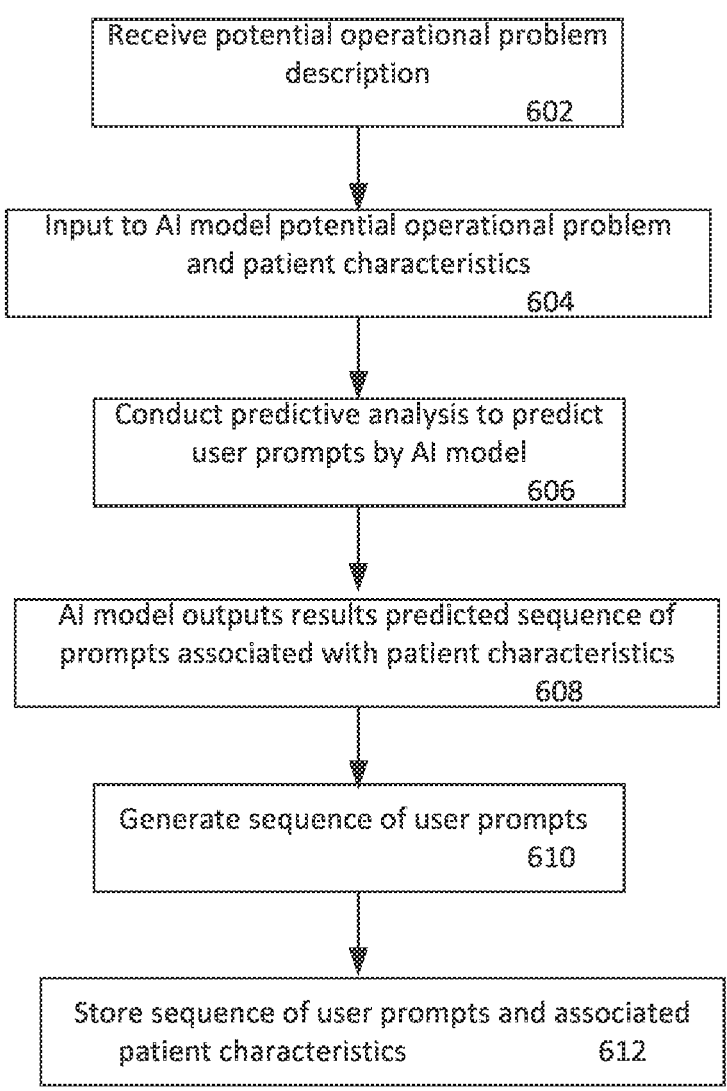

FIG. 6A shows a flowchart of an example method 600 to employ the prompt construct AI model. In block 602, a description of a potential operational problem of a type of medical device is received. The potential operational problem may be obtained by various sources, such as a user entering an operational problem into a user interface of a computing device. The potential operational problem may also be retrieved from past operational problems in stored global patient experience data for the type of medical device, or other such sources, such as from the medical device manufacturer or entities providing technical support for the medical device.

In some implementations, the global patient experience data may include prior key prompts, which were presented to prior patients as a last user prompt before it was detected that the operational problem was resolved. It may be considered that a key prompt was previously successful in resolving a same or similar operation problem for the type of medical device.

In block 604, data is inputted into the prompt construct AI model. The data includes the potential operational problem from block 602 and potential patient characteristics. The potential patient characteristics may be obtained from various sources. For example, potential characteristics data may be generated by processing global patient specific data of prior patients who have experienced using the type of medical device or who have experienced attempting to troubleshoot the same, similar, or other operational problems with the type of medical device. Such processing may include sorting and extracting the global patient specific data into particular categories. In some implementations, potential patient characteristics may be sourced from the manufacturer of the medical device, healthcare providers who prescribed the type of medical device, marketing resources, etc. Examples of potential patient characteristics may include at least some global patient specific data, such as patient demographics, patient medical conditions, possible patient temperaments, patient perception abilities/sensitivities (e.g., sensory, cognitive, or behavioral issues), physical movement abilities, possible patient current statuses (such as active in motion, being still, bathing, cleaning the medical device, sleeping, engaging in a particular exercise or activity (e.g. driving), or showing signs of stress), etc.

Other data may be inputted to the AI model as well. Certain requirements that the AI model follow may be entered. For example, a requirement may include that each user prompt of the sequence of user prompts of the output result is individually addressable to resolve the operational problem.

In block 606, the prompt construct AI model conducts predictive analysis to predict one or more sequences of user prompts to address the potential operational problem. The sequences of user prompts may correspond to particular potential patient characteristics.

In some implementations, the predictive analysis also includes predicting and outputting results for an output modality and/or output characteristic for each sequence of user prompts or for each user prompt in a sequence. The AI model can also consider the input of potential patient characteristics in predicting output modalities and output characteristics. The AI model predicts an output modality and/or output characteristic that may facilitate a user to follow a sequence of user prompts or individual user prompts. Some examples of output characteristic include volume, tone, text size or font, display brightness, white on black text, color, frequency of outputting sequential user prompts, and prompt language.

In such approaches, the output modality and/or the output characteristic is/are generated to correspond with one or more user prompts of the sequence of user prompts, based on output results of the AI model. The output modality and/or the output characteristic associated with the sequence of user prompts are stored for future use in selecting output modalities/output characteristics for particular patients.

In block 608, the AI model outputs results predicted sequence of user prompts associated with patient characteristics In block 610, at least one sequence of user prompts are generated based, at least in part, on the AI model output results. In some implementations, the user prompts of a sequence are arranged into a data structure for storing the sequence of user prompts in the data structure or storing references to each user prompt of the data structure. For example, the references may indicate a location of a user prompt in a data structure.

Some data structures are in the form of a hierarchical decision tree having a user prompt as each node of the tree. The decision tree may be constructed such that various paths to next nodes may be determined based at least in part on path selection criteria. Examples of path selection criteria can include patient specific factor, a result of an immediately prior operational problem check, prior user input, and patient specific experience data (e.g., descriptions of past patient experiences in troubleshooting a same or similar type of medical device by following a particular prompt).

In block 612, the sequence(s) of user prompts is/are stored along with the associated patient characteristics as well as output modalities and output characteristics.

The steps described in FIG. 6*a* may be performed by a troubleshooting system having one or more computer devices with an interface that receives the description of a potential operational and other input data. The computing device has one or more processors and logic encoded in one or more non-transitory media for execution by the processor(s). The steps are performed when the logic is executed.

The steps of the troubleshooting process 600 may be performed by components of the medical device troubleshooting system, and may be performed under the control of one or more computer systems configured with executable instructions and/or other data, and may be implemented as executable instructions executing collectively on one or more processors. For example the prompt predictor 128 shown in FIG. 1. The process 600 may also be performed as a service of a cloud server. In some implementations, troubleshooting process 600 may include additional steps or less steps, and the steps may be performed in various orders.

Figure 6B:
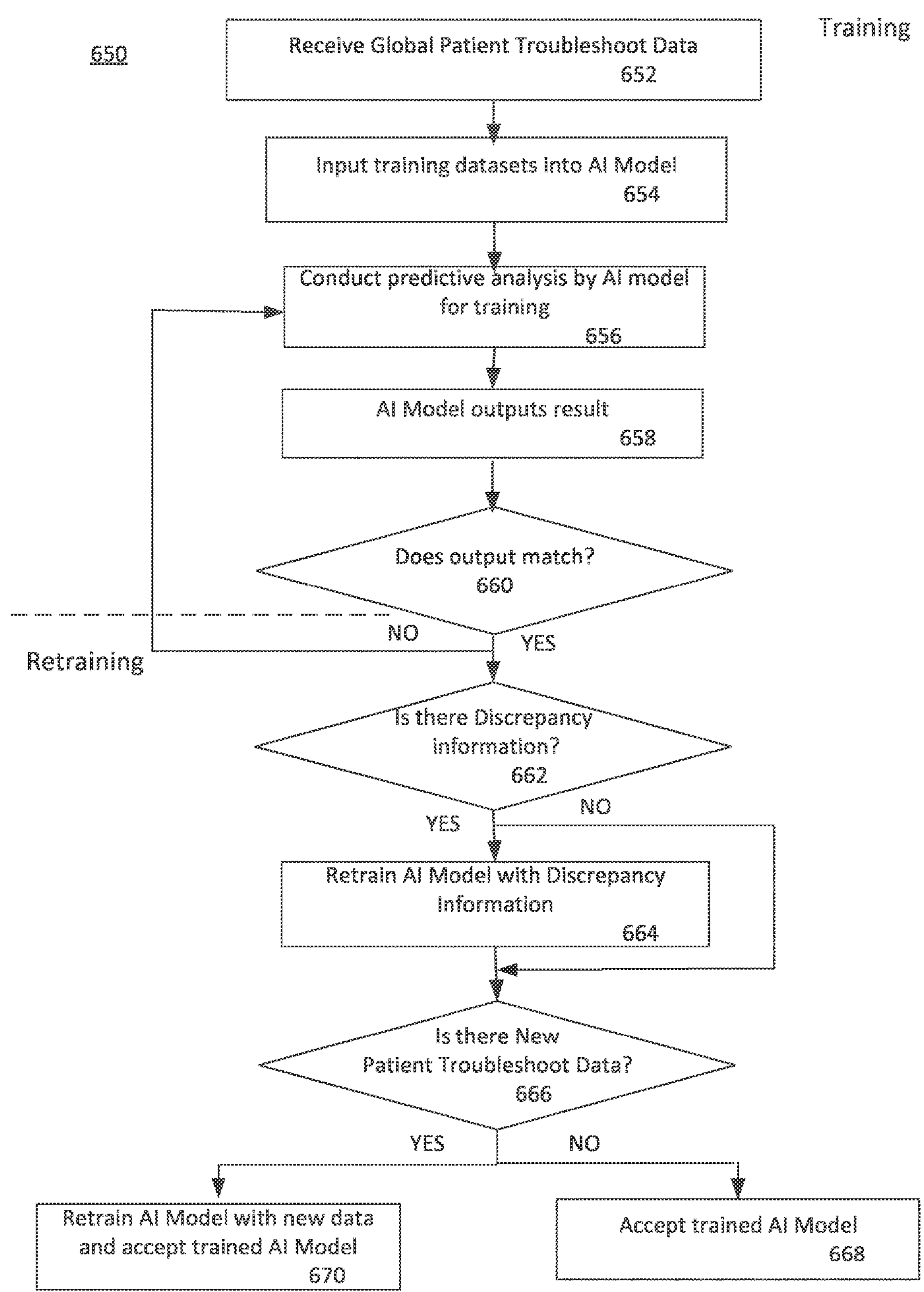

FIG. 6B shows a flowchart of an example method 650 to train and retrain the predictive AI models, including the prompt selector AI model and prompt construct AI model described above. In some implementations, the techniques to train the AI model may employ supervised classification algorithms, such as logistic regression algorithms. In some implementations, unsupervised or semi-supervised techniques may be employed.

In block 652, global patient experience data for previous patients, is received or otherwise accessed. For example the global patient experience data may include data on other patient encounters of the same or similar operational problem, the prompts presented to such other patients, the results of the prompts in resolving the operational problem, output modalities and output characteristics associated with the prompts, global patient specific data, etc. The global patient specific data may be stored for privacy without identifying information that would identify a particular patient.

In some implementations, global patient specific data may be also received and processed to determine the patient characteristic data that may be inputted as training datasets. The global patient specific data and patient characteristics are described above with regard to FIG. 6A for a prompt construct AI model.

In block 654, training datasets including operational problems are inputted into the AI mode. The training datasets may also include the global patient experience data and/or global patient specific data. For prompt construct AI models, training datasets may further include patient characteristics of the previous patients associated with the global patient experience data. In some implementations of prompt selector AI models, the training dataset(s) may include patient specific history experience from prior use of the medical device by the subject patient. In such cases, the patient specific history data may be associated with increased weight than global patient experience data for training of the AI model directed for use with the subject patient.

In some implementations, the data may be associated with labels of the operational problems and prompts. The training dataset may be processed prior to input to the AI model for training.

In block 656, the AI model conducts predictive analysis using the training dataset. The training of the AI model may include determining patterns in the previous patient data that leads to successful (positive results) and/or unsuccessful (negative results) troubleshooting. Based on the analysis, the AI model outputs a result of the analysis, in block 658.

In the case of a prompt construct AI model, the output result includes a predicted sequence of user prompts given potential patient characteristics, the potential operational problem for a type of medical device, and global patient experience data. Each user prompt provides a different instruction for a user to individually resolve the operational problem while the medical device is in use by a patient.

In the case of a prompt selector AI model, the output result includes a predicted sequence of user prompts or a particular user prompt that is determined to facilitate the user to successfully troubleshoot the subject operational problem of the medical device.

In decision block 660, the output result is compared with the training dataset inputted into the AI model and predetermined expected output result, to determine whether the output result matches. The predetermined expected output result may be determined by global patient experience data showing successful/unsuccessful use of user prompts or sequences of user prompts. It is determined whether a threshold of success is achieved by the output result in resolving the operational problem. The threshold of success may specify that some value equal to or less than 100% accuracy (such as 80%-90% success rate) is acceptable output results to be used. In some implementations, the output result may be used to dynamically change and enhance stored prompt sequences based on previous global prompting results If it is decided in decision block 660 that the output results match the training datasets to meet the threshold of success, the process continues. If there is a finding that the output results fail to match according to the threshold of success, the AI model is retrained by returning to block 606 and conducting predictive analysis again until the output result matches the training dataset. If a match is not achieved after a threshold number of tries, the analysis algorithm and/or training dataset may be assessed to find a solution to the failures.

In decision block 662, it is determined whether there is discrepancy information from prior AI model output results, in which the output of particular prompts was found to fail a threshold level of success in rectifying a same or similar operational problem. Discrepancy information may include feedback from an external support resource, user survey data, recordings of patient history experience, etc. The discrepancy information may be used for retraining in block 664. After discrepancy information retraining is complete, the process proceeds to decision block 666 described below.

If no discrepancy information is received, the process skips the discrepancy information retraining and continues to decision block 666 to determine if new data is available. As the AI models are used for new patients, the pool of patient experience data grows. For example, overtime, it may be found that global patient specific data may call for different user prompts. For example, patient characteristics including certain demographics such as gender, weight, age, preferred language, or other patient characteristics may indicate that the patient may respond better to particular prompt sequences.

The new prompt experience data is used for retraining in block 670 to increase accuracy of the AI models. Prompt sequences, such as changing an order of prompts, adding or subtracting prompts, rewording prompts, etc., may be dynamically changed based on retraining of the AI model. Where no new training data is available, in block 668, the AI model is accepted as being trained for use.

Some or all of the training/retraining process 650, or any other processes described herein, or variations and/or combinations of those processes, may be performed under the control of one or more computer systems configured with executable instructions and/or other data, and may be implemented as executable instructions executing collectively on one or more processors. In some implementations, training/retraining process 650 may include additional steps or less steps. In some implementations, the steps may be performed in various orders.

Figure 7:
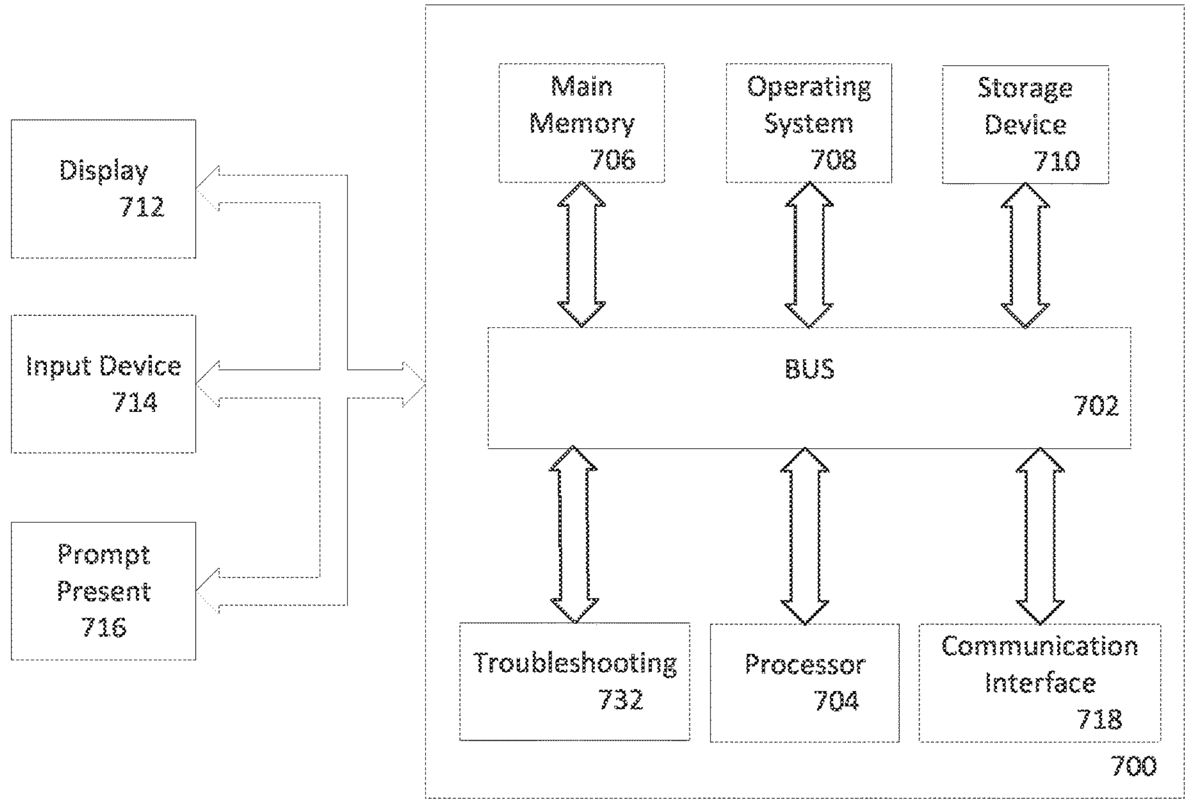
FIG. 7 is a block diagram illustrating an example computing device upon which one or more of the medical device troubleshooting processes may be implemented, in accordance with some implementations.

FIG. 7 shows an example computing device 700, which may implement some of the medical device troubleshooting processes described herein. The computer device 700 may include memory 706, processor 704, and communication (Input/Output) interface 718. The various elements of the client computing device 700 are shown in FIG. 7 as discrete/separate elements for purposes of illustration and explanation. According to some embodiments, it is possible to combine some of these elements into a single element or device. Additional components may also be included in the computing device.

The memory 706 of the client computing device 700 is for storing information within the client computing device 700. Memory 706 may be a random access memory (RAM) or other dynamic storage device, coupled to a bus for storing information and instructions to be executed by the processor 704. The memory 706 may also be used for storing temporary variables or other intermediate information during execution of instructions to be executed by the processor 704.

Such instructions, when stored in non-transitory storage media accessible to the processor 704, render the client computer system 700 into a special-purpose machine that is customized to perform the operations specified in the instructions.

The memory 706 may be any suitable data storage, memory and/or non-transitory computer-readable storage media, including electronic storage devices such as random-access memory (RAM), read-only memory (ROM), magnetic storage device (hard disk drive or the like), flash, optical storage device (CD, DVD or the like), magnetic or optical disk, or other tangible media suitable for storing instructions (e.g., program or software instructions) for execution by the processor 704. For example, a tangible medium such as a hardware storage device can be used to store the control logic, which can include executable instructions. The instructions can also be contained in, and provided as, an electronic signal, for example in the form of software as a service (SaaS) delivered from a server (e.g., a distributed system and/or a cloud computing system).

Storage device (data store) 710 may store various data including prompt sequence data structures, patient specific history experience data, global patient experience data, patient specific information, patient specific factors, an AI model repository for storing, aggregating, updating, managing and retrieving the trained AI models applications, and other data.

At least a portion of the information may also be stored on a disk drive or other computer readable storage device (not shown) within the client computing device 700. Such storage device include a floppy disk device, a hard disk device, an optical disk device, or a tape device, digital cards, a flash memory or other similar solid state memory device, or an array of devices.

Various modules or other computer programs, also referred to as programs, software, software applications or code, are stored within memory 706 and contain instructions that, when executed, perform one or more methods, such as those described herein. The computer program may be tangibly embodied in an information carrier such as computer or machine readable medium, for example, the memory 706, storage device or memory on processor 704. A machine readable medium is any computer program product, apparatus or device used to provide machine instructions or data to a programmable processor. Troubleshooting module(s) 732 may be provided to perform the processes described herein, such as in FIG. 4.

Any suitable programming languages and programming techniques may be used to implement the routines of particular embodiments. Different programming techniques may be employed such as procedural or object-oriented. The routines may execute on a single processing device or multiple processors. Although the steps, operations, or computations may be presented in a specific order, the order may be changed in different particular embodiments. In some particular embodiments, multiple steps shown as sequential in this specification may be performed at the same time. A number of implementations have been described. Features described with conditional language may describe implementations that are optional. The functional blocks, methods, devices, and systems described in the present disclosure may be integrated or divided into different combinations of systems, devices, and functional blocks as would be known to those skilled in the art.

The client computing device 700 may implement the techniques described herein using customized hard-wired logic, one or more ASICs or FPGAs, firmware and/or program logic which in combination with the computer system causes or programs the client computing device 700 to be a special-purpose machine. According to one implementation, the techniques herein are performed by the client computing device 700 in response to the processor 704 executing one or more sequences of one or more instructions contained in the memory 706. Such instructions may be read into the memory 706 from another storage medium. Execution of the sequences of instructions contained in the memory 706 causes the processor 704 to perform the process steps described herein.

In alternative implementations, one or more methods can be implemented in hardware (logic gates, etc.), or in a combination of hardware and software. Example hardware can be programmable processors (e.g. Field-Programmable Gate Array (FPGA), Complex Programmable Logic Device), general purpose processors, graphics processing units (GPUs), Application Specific Integrated Circuits (ASICs), and the like. One or more methods can be performed as part of or component of an application running on the system, or as an application or software running in conjunction with other applications and operating system 712.

The term "storage media" as used herein refers to any non-transitory media that store data and/or instructions that cause a machine to operate in a specific fashion. Such storage media may include non-volatile media and/or volatile media. Non-volatile media includes, for example, optical or magnetic disks. Volatile media includes dynamic memory, such as the memory 706. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, an EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire, and fiber optics, including the wires that include the bus. Transmission media can also take the form of acoustic or light waves, such as those generated during radio-wave and infra-red data communications.

Various forms of media may be involved in carrying one or more sequences of one or more instructions to the processor 704 for execution. For example, the instructions may initially be carried on a magnetic disk or solid state drive of a remote computer. The remote computer can load the instructions into its dynamic memory and send the instructions over a network connection. A modem or network interface local to the client computing device 700 can receive the data. The bus carries the data to the memory 706, from which the processor 704 retrieves and executes the instructions. The instructions received by the memory 706 may optionally be stored on a storage device either before or after execution by the processor 704.

Client computing device 700 further includes operating system 708, which may be stored in memory 706. Any operating system 708, e.g., mobile operating system, that is supports the matching processes described herein performed by the client computing device 700 may be employed.

The processor 704 may process instruction for execution within the client computing device 700 including instructions stored in memory 706 or on the data store 710. The processor 704 may coordinate computing device components, e.g. applications, wireless or wired communication through interfaces, etc. In some implementations, multiple processors and buses may be used.

The processor 704 may be implemented as a chipset of chips that include separate and multiple analog digital processors. The processor may also be implemented using various architectures. For example, the processor 704 may be a CISC (Complex Instruction Set Computer) processor, RISC (Reduced Instruction Set Computer) processor or MISC (Minimal Instruction Set Computer) processor, mobile device processors. etc.

The "processor" as used herein, includes any suitable hardware and/or software system, mechanism or component that processes data, signals or other information. A processor may include a system with a general-purpose central processing unit, multiple processing units, dedicated circuitry for achieving functionality, or other systems. Processing need not be limited to a geographic location, or have temporal limitations. For example, a processor may perform its functions in "real-time," "offline," in a "batch mode," etc. Portions of processing may be performed at different times and at different locations, by different (or the same) processing systems.

The Input/Output (I/O) interface 718 can interface to other input and output devices. In some implementations, the I/O interface 718 can connect to interface devices such as input devices (keyboard, pointing device, touchscreen, microphone, camera, scanner, sensors, etc.) and/or output devices (display devices, speaker devices, printers, motors, etc.). Some implementations can provide a microphone for capturing sound (e.g., as a part of captured images, voice commands, etc.), audio speaker devices for outputting sound, or other input and output devices.

The computer system 700 may be coupled via the bus 702 to a display 712, such as a computer monitor, for displaying a GUI with the prompts and other prompt presentation device(s) 716 such as a speaker and vibration actuator. An input device 714, such as a microphone, alphanumeric and other keys, etc., is coupled to the bus 702 for communicating information and command selections to the processor 704. Another type of user input device is a cursor control, such as a mouse, a trackball, or cursor direction keys for communicating direction information and command selections to the processor 704 and for controlling cursor movement on the display 712.

The devices and/or systems described in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described above. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations that may be provided within at least one non-transitory, tangible, computer readable medium for execution by the one or more processors. An economy is achieved in that flowcharts as in FIGS. 4, 5, and 6 are used to describe both programs, and also methods. So, while flowcharts described methods in terms of boxes, they also concurrently describe programs.

Other implementations include combinations and sub-combinations of features described or shown in the drawings herein, including for example, implementations that are equivalent to: providing or applying a feature in a different order than in a described implementation, extracting an individual feature from one and inserting such feature into another implementations; removing one or more features from an implementation; or both removing one or more features from an implementation and adding one or more features extracted from one or more other implementations, while providing the advantages of the features incorporated in such combinations and sub-combinations. As used in this paragraph, feature or features can refer to the structures and/or functions of an apparatus, article of manufacture or system, and/or the steps, acts, or modalities of a method.

We claim:

1. A method for resolving an operational problem of a medical device to treat a medical condition of a patient, the method comprising:

receiving signals, if available, from a sensor associated with the medical device;

assessing the signals in response to signals being available and determining that no signals are received in response to signals not being available, to detect an operational problem of the medical device that causes the medical device to operate below a standard operating level to administer a shock treatment for a cardiovascular medical condition of the patient;

in response to detecting the operational problem, initiating a troubleshooting session, in which a series of different individual user troubleshooting prompts is generated configured for the patient and specifying actions for the patient to perform to resolve the detected operational problem, the troubleshooting session, including:

assessing patient specific data to determine one or more patient specific factors that impact the patient in receiving or responding to the user troubleshooting prompts, including at least one of: a current patient activity other than the patient responding to the user prompts, a patient temperament, and a patient trait;

selecting an initial user troubleshooting prompt based, at least in part, on the one or more patient specific factors;

outputting the initial user troubleshooting prompt to the patient;

selecting a next user troubleshooting prompt that has different wording than the initial user troubleshooting prompt and wherein the different wording accommodates a patient need to assist the patient in responding to the next user troubleshooting prompt indicated by the one or more patient specific factors, wherein the selecting includes:

detecting a current patient status;

accessing two or more types of user troubleshooting prompts related to different patient statuses; and retrieving the next troubleshooting prompt that corresponds to the current patient status;

outputting the selected next user troubleshooting prompt to the patient; and iteratively repeating: the assessing of the signals or the determining that no signals are received, the selecting of the next user troubleshooting prompt each of which has different wording from each prior user troubleshooting prompt in the trouble shooting session and that accommodates the patient need, and the outputting of the selected next user troubleshooting prompt, until at least one stopping event occurs;

detecting that the operational problem is resolved; and administering, by the medical device, the shock treatment for the cardiovascular medical condition by meeting the standard operating level.

2. The method of claim 1, wherein the outputting of the initial troubleshooting prompt and the selected next user troubleshooting prompt includes selecting at least one output modality to further accommodate the patient need.

3. The method of claim 1, wherein the one or more patient specific factors includes the current patient activity detected by the medical device, and the method further comprising:

selecting a first stored sequence of user troubleshooting prompts associated with a same or similar operational problem, wherein selecting the stored sequence of user troubleshooting prompts is based, at least in part, on the patient current activity; and during the troubleshooting session, dynamically reselecting a second stored sequence of user troubleshooting prompts or reselecting a different next user troubleshooting prompt based, at least in part, on the medical device detecting a change in the patient current activity other than the patient responding to the user troubleshooting prompts.

4. The method of claim 1, further comprising:

applying an artificial intelligence model trained, at least in part, on global patient experience data, to output sequences of user troubleshooting prompts associated with various operational problems;

storing the outputted sequence of user troubleshooting prompts; and selecting a sequence of user troubleshooting prompts from the stored sequence of user troubleshooting prompts, based at least in part, on the one or more patient specific factors, wherein selecting the user troubleshooting prompts is further based, at least in part, on the selected sequence of user troubleshooting prompts.

5. The method of claim 1, wherein selecting an initial user troubleshooting prompt of the user troubleshooting prompts is further based on one or more prior successful user troubleshooting prompts in previous troubleshooting sessions for a same or similar operational problem by the patient.

6. The method of claim 1, wherein the stopping event includes: a predefined time for the troubleshooting session is reached or a threshold number of user troubleshooting prompts are outputted without resolution of the operational problem.

7. A medical device troubleshooting system for resolving an operational problem of a medical device to treat a medical condition of a patient, comprising:

the medical device in use by the patient, the medical device including at least one sensor to monitor a parameter associated with health of the patient and to generate signals based on the monitored parameter; and at least one computing device including at least one processor configured for:

detecting the operational problem of the medical device based on the signals, wherein the operational problem causes the medical device to operate below a standard operating level to administer a shock treatment for a cardiovascular a medical condition of the patient; and in response to the detected operational problem, initiating a troubleshooting session, in which a series of different individual user troubleshooting prompts is generated configured for the patient and specifying actions for the patient to perform to resolve the detected operational problem, including:

assessing patient specific data to determine one or more patient specific factors that impact the patient receiving or responding to the user troubleshooting prompts, including at least one of: a current patient activity other than the patient responding to the user troubleshooting prompts, a patient temperament, and a patient trait;

selecting an initial user troubleshooting prompt that has different wording than the initial user troubleshooting prompt and wherein the different wording accommodates a patient need to assist the patient in responding to the next user troubleshooting prompt indicated by the one or more patient specific factors, wherein the selecting includes:

detecting a current patient status;

accessing two or more types of user troubleshooting prompts related to different patient statuses; and retrieving the next troubleshooting prompt that corresponds to the current patient status;

outputting the initial user troubleshooting prompt to the patient;

selecting a next user troubleshooting prompt based, at least in part, on the one or more patient specific factors;

outputting the selected next user troubleshooting prompt to the patient; and iteratively repeating: the assessing of the signals or the determining that no signals are received, the selecting of the next user troubleshooting prompt each of which has different wording from each prior user troubleshooting prompt in the trouble shooting session and that accommodates the patient need, and the outputting of the selected next, until at least one stopping event occurs; and detecting that the operational problem is resolved; and administering, by the medical device, the shock treatment for the cardiovascular medical condition by meeting the standard operating level.

8. The system of claim 7, wherein the outputting of the initial user troubleshooting prompt and the selected next user troubleshooting prompt includes selecting at least one output modality to further accommodate the patient need.

9. The system of claim 7, wherein the one or more patient specific factors includes the current patient activity detected by the medical device, and the system further comprising a one or more sensors to detect the current patient activity, wherein the troubleshooting session further includes:

selecting a first stored sequence of user troubleshooting prompts associated with a same or similar operational problem, wherein selecting the stored sequence of user troubleshooting prompts is based, at least in part, on the patient current activity; and dynamically reselecting a second stored sequence of user troubleshooting prompts based, at least in part, on the medical device detecting a change in the patient current activity other than the patient responding to the user troubleshooting prompts.

10. The system of claim 7, wherein the troubleshooting session further includes:

selecting a sequence of user troubleshooting prompts from a stored sequence of user troubleshooting prompts, based at least in part, on the one or more patient specific factors, wherein the stored sequence of user troubleshooting prompts is outputted from an artificial intelligence model trained, at least in part, on global patient experience data, wherein selecting the user troubleshooting prompts is further based, at least in part, on the selected sequence of user troubleshooting prompts.

11. The system of claim 7, wherein selecting the one or more initial user troubleshooting prompts is further based on one or more prior successful user troubleshooting prompts in previous troubleshooting of a same or similar operational problem by the patient.

12. The system of claim 7, wherein the stopping event includes a predefined time for the troubleshooting session is reached or a threshold number of user troubleshooting prompts are outputted without resolution of the operational problem.

13. The system of claim 12, the troubleshooting session further comprises:

detecting the threshold number of user troubleshooting prompts are outputted without resolution; and contacting an external support or instructing the user to contact the external support.

14. A method for resolving an operational problem of a wearable medical device to use for a cardiovascular condition of a patient, the method comprising:

receiving electrocardiogram (ECG) signals, if available, from one or more electrodes coupled to a wearable article of the medical device that treats a cardiovascular condition of the patient;

assessing the ECG signals in response to receiving ECG signals and determining that no ECG signals are received if no ECG signals are available, to detect an operational problem of the medical device that hinders the function of at least one of the one or more electrodes to administer a shock treatment for the cardiovascular condition at a standard operating level; and in response to detecting the operational problem, initiating a troubleshooting session, in which a series of different individual user troubleshooting prompts is generated configured for the patient and specifying actions for the patient to perform to resolve the detected operational problem, including:

assessing patient specific data to determine one or more patient specific factors that impact the patient receiving or responding to the user troubleshooting prompts, including at least one of: a current patient activity other than the patient responding to the user troubleshooting prompts, a patient temperament, and a patient trait;

selecting a stored sequence of user troubleshooting prompts associated with a same or similar operational problem, wherein selecting the stored sequence of user troubleshooting prompts is based, at least in part, on the one or more patient specific factors;

selecting an initial user troubleshooting prompt from the stored sequence of user troubleshooting prompts with one or more instructions to assist the patient in resolving the operational problem, based, at least in part, on the one or more patient specific factors; and outputting the selected initial user troubleshooting prompt;

iteratively repeating: the assessing of the ECG signals or the determining that no ECG signals are received, selecting a next user troubleshooting prompt that has different wording than the initial user troubleshooting prompt and wherein the different wording accommodates a patient need in responding to the next user troubleshooting prompt indicated by the one or more patient specific factors, and outputting the selected next user troubleshooting prompt until at least one stopping event occurs, wherein the selecting includes:

detecting a current patient status;

accessing two or more types of user troubleshooting prompts related to different patient statuses; and retrieving the next troubleshooting prompt that corresponds to the current patient status;

detecting that the operational problem is resolved; and administering, by the medical device, shock treatment for the cardiovascular condition by meeting the standard operating level.

15. The method of claim 14, wherein at least one of the user troubleshooting prompts includes instructions for the user to manipulate the wearable article or at least one of the one or more electrodes.

16. The method of claim 14, wherein the one or more patient specific factors include the patient current activity detected by the medical device, and wherein after a first iteration, the method further comprising:

dynamically reselecting a different stored sequence of user troubleshooting prompts based, at least in part, on the medical device detecting the change in the patient current activity other than the patient responding to the user troubleshooting prompts.

17. The method of claim 14, further comprising:

applying an artificial intelligence model trained, at least in part, on global patient experience data, to output sequences of user troubleshooting prompts associated with various operational problems;

storing the outputted sequence of user troubleshooting prompts, wherein selecting the sequence of user troubleshooting prompts is from the stored sequence of user troubleshooting prompts, based at least in part, on the one or more patient specific factors, wherein selecting the user troubleshooting prompts is further based, at least in part, on the selected sequence of user troubleshooting prompts.

18. The method of claim 1, wherein the selecting of the next user troubleshooting prompt includes selecting a user troubleshooting prompt for the user to perform a same action of a same approach to resolve the operational problem as an approach of at least one prior user troubleshooting prompt outputted during the troubleshooting session that did not resolve the operational problem.

19. The method of claim 1, wherein the one or more patient specific factors includes the current patient activity and wherein selecting the next user troubleshooting prompt includes: directing the patient to change the current patient activity, and/or pausing the outputting of the user troubleshooting prompt while the patient is performing the current patient activity.

20. The method of claim 1, wherein detecting the current patient status includes detecting that the patient is in-motion or the patient is stationary, wherein the two or more types of user troubleshooting prompts include an in-motion type and a stationary normal type, and wherein retrieving the next troubleshooting prompt includes selecting the in-motion type prompt or the stationary normal type prompt.

* * * * *